(12) United States Patent
Miki et al.

(10) Patent No.: US 10,190,898 B2
(45) Date of Patent: Jan. 29, 2019

(54) PHYSICAL-QUANTITY DETECTION DEVICE

(71) Applicant: Hitachi Automotive Systems, Ltd., Hitachinaka-shi, Ibaraki (JP)

(72) Inventors: Takahiro Miki, Hitachinaka (JP); Takayuki Yogo, Hitachinaka (JP); Hiroaki Hoshika, Hitachinaka (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 28 days.

(21) Appl. No.: 15/329,873

(22) PCT Filed: Jun. 15, 2015

(86) PCT No.: PCT/JP2015/067106
§ 371 (c)(1),
(2) Date: Jan. 27, 2017

(87) PCT Pub. No.: WO2016/017298
PCT Pub. Date: Feb. 4, 2016

(65) Prior Publication Data
US 2017/0248455 A1    Aug. 31, 2017

(30) Foreign Application Priority Data

Jul. 30, 2014    (JP) ................. 2014-154683

(51) Int. Cl.
*G01F 5/00*    (2006.01)
*F02M 35/10*    (2006.01)
(Continued)

(52) U.S. Cl.
CPC ....... *G01F 1/6845* (2013.01); *F02M 35/1038* (2013.01); *F02M 35/10386* (2013.01);
(Continued)

(58) Field of Classification Search
CPC ......... F02M 35/1038; F02M 35/10386; F02M 35/10393; G01F 1/684; G01F 1/696; G01F 1/6845; G01N 33/0022
See application file for complete search history.

(56) References Cited

U.S. PATENT DOCUMENTS

2008/0163683 A1    7/2008    Becke et al.
2010/0001956 A1    1/2010    Choi
(Continued)

FOREIGN PATENT DOCUMENTS

| CN | 101216331 A | 7/2008 |
| CN | 102280420 A | 12/2011 |

(Continued)

OTHER PUBLICATIONS

International Search Report (PCT/ISA/210) issued in PCT Application No. PCT/JP2015/067106 dated Sep. 29, 2015 with English-language translation (four (4) pages).
(Continued)

*Primary Examiner* — Paul M. West
(74) *Attorney, Agent, or Firm* — Crowell & Moring LLP

(57) ABSTRACT

The purpose of this invention is to obtain a physical-quantity detection device, the external shape of the housing of which can be reduced in size. Said physical-quantity detection device, which detects a plurality of physical quantities of a gas being measured that flows through a main channel, is characterized by having a housing positioned inside said main channel, a circuit board insert-molded into said housing, and a plurality of detection sensors mounted on both sides of the circuit board.

8 Claims, 15 Drawing Sheets

(51) Int. Cl.
*G01F 1/684* (2006.01)
*G01F 1/696* (2006.01)
*G01N 33/00* (2006.01)

(52) U.S. Cl.
CPC ....... *F02M 35/10393* (2013.01); *G01F 1/684* (2013.01); *G01F 1/6842* (2013.01); *G01F 1/696* (2013.01); *G01F 5/00* (2013.01); *G01N 33/0022* (2013.01)

(56) References Cited

U.S. PATENT DOCUMENTS

| | | |
|---|---|---|
| 2010/0031737 A1 | 2/2010 | Saito et al. |
| 2011/0072894 A1 | 3/2011 | Saito et al. |
| 2011/0298112 A1 | 12/2011 | Mori |
| 2012/0198925 A1 | 8/2012 | Saito et al. |
| 2013/0036806 A1 | 2/2013 | Kohno |
| 2013/0283895 A1 | 10/2013 | Etherington et al. |
| 2014/0139240 A1 | 5/2014 | Burger |
| 2015/0354512 A1* | 12/2015 | Tsujii .................. G01F 1/6842 73/114.32 |

FOREIGN PATENT DOCUMENTS

| | | |
|---|---|---|
| CN | 103733518 A | 4/2014 |
| EP | 1 279 934 A2 | 1/2003 |
| EP | 2 306 161 A1 | 4/2011 |
| JP | 6-265384 A | 9/1994 |
| JP | 9-53967 A | 2/1997 |
| JP | 2000-28411 A | 1/2000 |
| JP | 2001-8068 A | 1/2001 |
| JP | 2010-43883 A | 2/2010 |
| JP | 2010-151795 A | 7/2010 |
| JP | 2011-75357 A | 4/2011 |
| JP | 2012-163505 A | 8/2012 |
| JP | 2013-36892 A | 2/2013 |
| WO | WO 2013/187253 A1 | 12/2013 |

OTHER PUBLICATIONS

Japanese-language Written Opinion (PCT/ISA/237) issued in PCT Application No. PCT/JP2015/067106 dated Sep. 29, 2015 (four (4) pages).
Extended European Search Report issued in counterpart European Application No. 15828022.2 dated Nov. 10, 2017 (seven pages).
Chinese-language Office Action issued in counterpart Chinese Application No. 201580040266.1 dated Oct. 16, 2018 (eight (8) pages).

* cited by examiner

PHYSICAL-QUANTITY DETECTION DEVICE

TECHNICAL FIELD

The present invention relates to a physical quantity detection device which detects a physical quantity of an intake air of an internal combustion engine.

BACKGROUND ART

In an automobile field, a regulation on a fuel efficiency, $CO_2$ an exhaust gas (mainly nitrogen oxides (NOx), and particulate matters (PM)) becomes tighter every year, and a number of new control schemes for satisfying the regulation are considered as a future control on an internal combustion engine. Among them, a physical quantity detection device used in various types of controls becomes diverse. In particular, physical quantities such as an air, temperature, humidity, and pressure in an intake pipe for the connection to a combustion chamber of the internal combustion engine are necessarily measured with accuracy because the quantities directly influence on the fuel efficiency and an exhaust gas.

The regulation on the fuel efficiency, $CO_2$, and the exhaust gas are calculated and regulated on the basis of a running cycle represented as NEDC of Europe. For a future regulation, not only the regulation values but also a running cycle condition and an on-vehicle diagnosis system (OBD) regulation value are changed.

Presently, the physical quantity detection device to be inserted in the intake pipe generally measures mass flow rate, pressure, and temperature. However, a control using an absolute humidity (an amount of moisture in the air) is received a lot of attention as an internal combustion control in view of the above situation.

Since the moisture in the air affects a flame spread time in a combustion control of the internal combustion engine, a gasoline engine is degraded in combustion efficiency for example. In addition, there is known an influence of an emission increase of PM in a diesel engine as the combustion temperature is lowered.

Herein, the absolute humidity indicates an amount of moisture contained in the air (g gram/kg kilogram), and can be calculated from a temperature, a relative humidity, and a pressure in the air. On the other hand, the relative humidity indicates a ratio (% percent) of the amount of moisture in the air.

As described above, temperature and pressure sensors are used in the automobile field for a long time, but a sensor for measuring the relative humidity in the air flowing in the intake pipe are not much known. Presently, there are disclosures that the humidity sensor is integrally configured to an air flow rate detection device in the automobile field (see PTLs 1 to 3).

The air flow rate detection devices disclosed in PTLs 1 and 2 are integrated with an air flow rate sensor, a humidity sensor, and a pressure sensor. The air flow rate sensor is positioned in a bypass passage through which the air flowing in a main air passage (simply referred to as intake pipe) is taken, and is disposed in a terminal member formed of a metal material. The humidity sensor is positioned in a second bypass passage through which the air flowing in the bypass passage is taken, and mounted in an electronic printed-circuit board. Finally, the pressure sensor is disposed in a housing member. In other words, the respective physical quantity detection sensors are disposed in different members.

CITATION LIST

Patent Literature

PTL 1: JP 2010-43883 A
PTL 2: JP 2012-163505 A
PTL 3: JP 2013-36892 A

SUMMARY OF INVENTION

Technical Problem

In recent years, various technical improvements are achieved in the automobile field in order to improve an exhaust gas regulation, safety, comfort, and convenience in addition to fundamental performances of the vehicle. Thus, a wide variety of sensors are used for the technical improvement. Therefore, the number of wire harnesses connecting the sensors and an engine control unit (hereinafter, referred to as ECU) is also increased and complicated. Thus, there is a problem in a cost viewpoint and a space viewpoint in the engine room. Therefore, there is currently increasing demand for the physical quantity detection device in which the plurality of sensors and the control machine are integrated. The number of wire harnesses and a miniaturization are expected through the integration.

In the air flow rate detection device disclosed in PTLs 1 to 3, the air flow rate sensor, the pressure sensor, and the humidity sensor are disposed in different members and disposed in consideration of performance of each sensor, but there is room for improvement in size of a casing (hereinafter, referred to as housing).

First, the air flow rate detection device is disposed in the intake pipe used for the connection to the combustion chamber of the internal combustion engine, and a measurement unit of the housing where the sensor is disposed is mounted to be exposed in the intake pipe. Therefore, the housing causes a pressure loss with respect to the air in the intake pipe. In other words, when the size of the housing is increased, the pressure loss is increased, the amount of air introduces to the combustion chamber is reduced. An engine output is obtained by converting heat energy generated by a chemical reaction between the fuel and the air into kinetic energy. Therefore, a reduction of a maximum air flow rate in the combustion chamber caused by the pressure loss results in a reduction of the engine output. An increase of the pressure loss together with the maximum air flow rate influences even on a minimum air flow rate which can flow in the combustion chamber. In other words, the measurement accuracy in an ultra-low flow rate will be required for the air flow rate detection device in the future as the engine is miniaturized and also a bore diameter of the intake pipe is reduced.

In the air flow rate detection device, a flange and a connector which are formed integrally to the housing and fixedly supported to the intake pipe are exposed in the engine room while not being exposed in the intake pipe. The engine room is configured by an engine hood and a vehicle body, and various engine components are disposed therein. It is expected that the space is reduced still more in the future due to a miniaturization of the engine and a protection standard of a pedestrian head in recent years. Among them, the integration of the plurality of sensors in the air flow rate detection device is essentially considered for the size of the housing.

The invention has been made in view of the above problems, and an object thereof is to provide a physical quantity detection device in which the exterior of the housing can be miniaturized.

Solution to Problem

In the invention, a configuration described in claims will be employed for example in order to solve the problems. A physical quantity detection device according to the present invention detects a plurality of physical quantities of a measuring target gas flowing in a main passage, and includes: a housing that is disposed in the main passage; a printed circuit board that is formed to be inserted in the housing; and a plurality of detection sensors that are mounted on one surface and the other surface of the printed circuit board.

Advantageous Effects of Invention

According to the invention, the printed circuit board can be miniaturized by disposing a plurality of physical quantity detection sensors using both surfaces of the electronic printed-circuit board. In other words, a casing part of the physical quantity detection device can also be miniaturized along the miniaturization of the printed circuit board, resulting in securing the space of the engine room and reducing the pressure loss in the intake pipe which have been the problems. Further, advantages, configurations, and effects other than the above description will be cleared through the descriptions of the following embodiments.

BRIEF DESCRIPTION OF DRAWINGS

FIGS. 12A and 12B are diagrams for describing a structure of a sensor chamber, in which FIG. 12A is an enlarged view of the sensor chamber, and FIG. 12B is a cross-sectional view taken along a line D-D of FIG. 12A.

FIGS. 13A and 13B are diagrams for describing a structure of a sensor chamber according to another embodiment, in which FIG. 13A is an enlarged view of the sensor chamber, and FIG. 13B is a cross-sectional view taken along a line E-E of FIG. 13A.

FIGS. 14A and 14B are diagrams for describing a structure of a sensor chamber according to another embodiment, in which FIG. 14A is an enlarged view of the sensor chamber, and FIG. 14B is a cross-sectional view taken along a line F-F of FIG. 14A.

DESCRIPTION OF EMBODIMENTS

Figure 1:
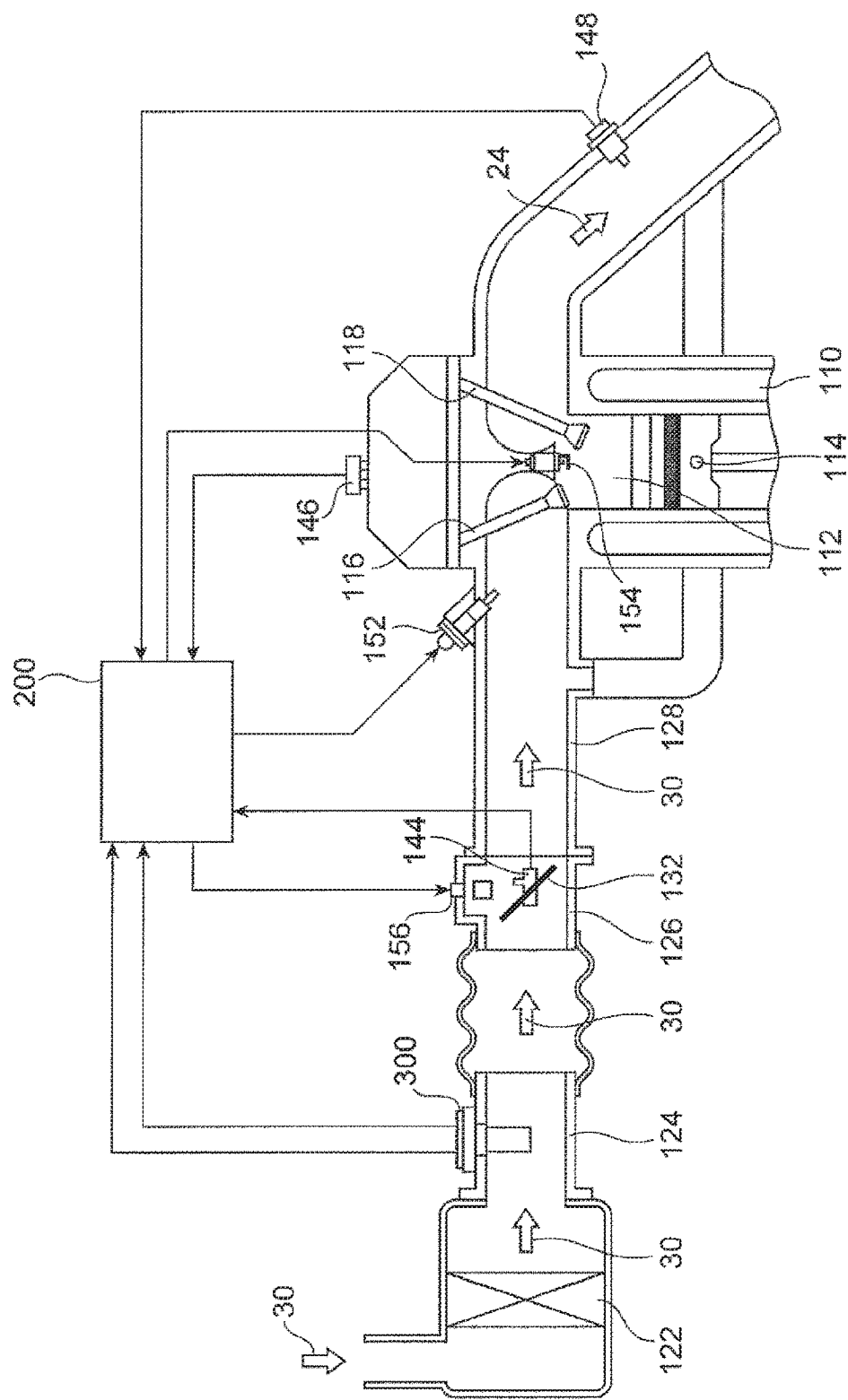
FIG. 1 is a system diagram illustrating an embodiment in which a physical quantity detection device according to the invention is used in an internal combustion engine control system.

Embodiments for implementing the invention (hereinafter, referred to as embodiments) to be described below solve various problems, which is desired for an actual product, and particularly solve various problems which should be required when a physical quantity of an intake air of a vehicle is used as a detection device, and various effects can be achieved. One of the problems to be solved by the following embodiments is the content shown in a column of "Technical Problem". In addition, one of the effects to be achieved by the following embodiments is the effect shown in a column of "Advantageous Effects of Invention". The various problems to be solved by the following embodiments and also the various effects to be achieved by the following embodiments will be described in the explanation of the embodiments. Therefore, the effects and the problems to be solved by the embodiments are described even in the content other than the content of the columns of "Technical Problem" and "Advantageous Effects of Invention".

In the following embodiments, the same symbols indicate the same configuration even in the different drawings, and draw the same operational effect. The configurations described already will be assigned only with the symbols in the drawings, and the descriptions thereof will not be repeated.

1. Embodiment of Physical Quantity Detection Device According to Invention Used in Internal Combustion Engine Control System FIG. 1 is a system diagram illustrating an embodiment in which a physical quantity detection device according to the invention is used in an internal combustion engine control system in which the fuel is injected in an electronic manner. The intake air is sucked as a measuring target gas 30 from an air cleaner 122 on the basis of an operation of an internal combustion engine 110 which is provided with an engine cylinder 112 and an engine piston 114, and is guided through a main passage 124 (for example, an intake body, a throttle body 126, and an intake manifold 128) to a combustion chamber of the engine cylinder 112.

A physical quantity of the measuring target gas (intake air) 30 guided to the combustion chamber is detected by a physical quantity detection device 300 according to the invention. The fuel is supplied by a fuel injection valve 152 on the basis of the detected physical quantity, and is guided to the combustion chamber in a state of being mixed with the intake air 20. Further, in this embodiment, the fuel injection valve 152 is provided in an intake port of the internal combustion engine. The fuel injected to the intake port forms a mixed gas together with the measuring target gas (intake air) 30, guided through an intake valve 116 to the combustion chamber, and combusted to generate mechanical energy.

In recent years, a method of using the fuel injection valve 152 mounted in a cylinder head of the internal combustion engine to directly injecting the fuel from the fuel injection valve 152 into each combustion chamber is employed in many vehicles as a method excellent in exhaust gas purification and in fuel efficiency. The physical quantity detection device 300 can use not only the method of injecting the fuel to the intake port of the internal combustion engine illustrated in FIG. 1 but also similarly the method of directly injecting the fuel into each combustion chamber. Both methods are substantially common in basic concept of a method of measuring control parameters including a method of using the physical quantity detection device 300 and a method of controlling the internal combustion engine including a fuel supply amount and an ignition time. As a representative of both methods, a method of injecting the fuel to the intake port is illustrated in FIG. 1.

The fuel and the air guided into the combustion chamber come into a fuel-air mixed state, and explosively combusted by spark ignition of an ignition plug 154, so that mechanical energy is generated. The combusted gas is guided from an exhaust valve 118 to an exhaust pipe, and discharged as an exhaust gas 24 from the exhaust pipe to the outside of the vehicle. A flow rate of the measuring target gas (intake air) 30 guided into the combustion chamber is controlled by a throttle valve 132 of which the opening is changed on the basis of an operation of an accelerator pedal. The fuel supply amount is controlled on the basis of the flow rate of the intake air guided into the combustion chamber, and a driver controls the opening of the throttle valve 132 to control the flow rate of the intake air guided into the combustion chamber, so that the mechanical energy generated by the internal combustion engine can be controlled.

1.1 Outline of Control of Internal Combustion Engine Control System

The physical quantities such as a flow rate, a temperature, a humidity, and a pressure of the measuring target gas (intake air) 30 taken in from the air cleaner 122 and flowing in the main passage 124 are detected by the physical quantity detection device 300. An electric signal indicating the physical quantity of the intake air is input from the physical quantity detection device 300 to a control device 200. In addition, the output of the throttle angle sensor 144 for measuring the opening of the throttle valve 132 is input to the control device 200, and also the output of a rotation angle sensor 146 is input to the control device 200 to measure positions and states of the engine piston 114, the intake valve 116, and the exhaust valve 118 of the internal combustion engine together with a rotation speed of the internal combustion engine. The output of an oxygen sensor 148 is input to the control device 200 to measure the state of a mixture ratio of the amounts of fuel and air from the state of the exhaust gas 24.

The control device 200 calculates a fuel injection amount and an ignition timing on the basis of a physical quantity of the intake air (the output) of the physical quantity detection device 300 and the rotation speed of the internal combustion engine measured from the output of the rotation angle sensor 146. On the basis of these calculation results, the fuel amount supplied from the fuel injection valve 152 and the ignition timing when the ignition plug 154 ignites are controlled. In practice, the fuel supply amount and the ignition timing are finely controlled on the basis of a state of changes in temperature and throttle angle detected by the physical quantity detection device 300, a stage of change in rotation speed of the engine, and a state of fuel ratio measured by the oxygen sensor 148. The control device 200 controls the amount of air bypassing the throttle valve 132 using an idle air control valve 156 in an idle operation mode of the internal combustion engine, and controls the rotation speed of the internal combustion engine in the idle operation mode.

1.2 Importance of Detection Accuracy Improvement of Physical Quantity Detection Device and Installation Environment of Physical Quantity Detection Device Both the fuel supply amount and the ignition timing, which are primary control quantities in the internal combustion engine, are calculated on the basis of the output of the physical quantity detection device 300 as main parameters. Therefore, improvement of detection accuracy of the physical quantity detection device 300, suppression of a change with time, and improvement of reliability are important for the improvement of control accuracy of the vehicle and for the securement of reliability.

Particularly, in recent years, a request for fuel saving of the vehicle is significantly increased, and a request for the exhaust gas purification is sign significantly increased. In response to these requests, it is extremely important to increase the detection accuracy of the physical quantity of the intake air detected by the physical quantity detection device 300. In addition, it is also important to keep a high reliability of the physical quantity detection device 300.

The vehicle equipped with the physical quantity detection device 300 is used under an environment having a large temperature variation, and also in the middle of rainy or snowy weather. In a case where an automobile runs on a snowy road, it becomes a running on a road sprinkled with an antifreezing agent. A countermeasure against the change in temperature in such an environment and against dust and contaminants are also desirably taken into consideration for the physical quantity detection device 300. Furthermore, the physical quantity detection device 300 is installed under an environment where the internal combustion engine vibrates. A high level of reliability is also required with respect to the vibration.

In addition, the physical quantity detection device 300 is mounted in an intake pipe which is affected by heating from the internal combustion engine. Therefore, the heat of the internal combustion engine is transferred onto the physical quantity detection device 300 through the intake pipe that is the main passage 124. The physical quantity detection device 300 is to detect the flow rate of the measuring target gas 30 through the heat transmission with respect to the measuring target gas 30, and thus it is important to suppress an influence of heat from the outside as much as possible.

The physical quantity detection device 300 mounted in the vehicle is provided not only simply to solve the problem described in the column of "Technical Problem" and to achieve the effect described in the column of "Advantageous Effects of Invention" as described below, but also to solve various problems required to be solved as a product in sufficient consideration of the above-described various problems and to achieve various effects as described below. The specific problems to be solved and the specific effect to be achieved through the physical quantity detector device 300 will be described in the embodiments described below.

2. Configuration of Physical Quantity Detection Device 300

2.1 Exterior Structure of Physical Quantity Detection Device 300

Figure 2:
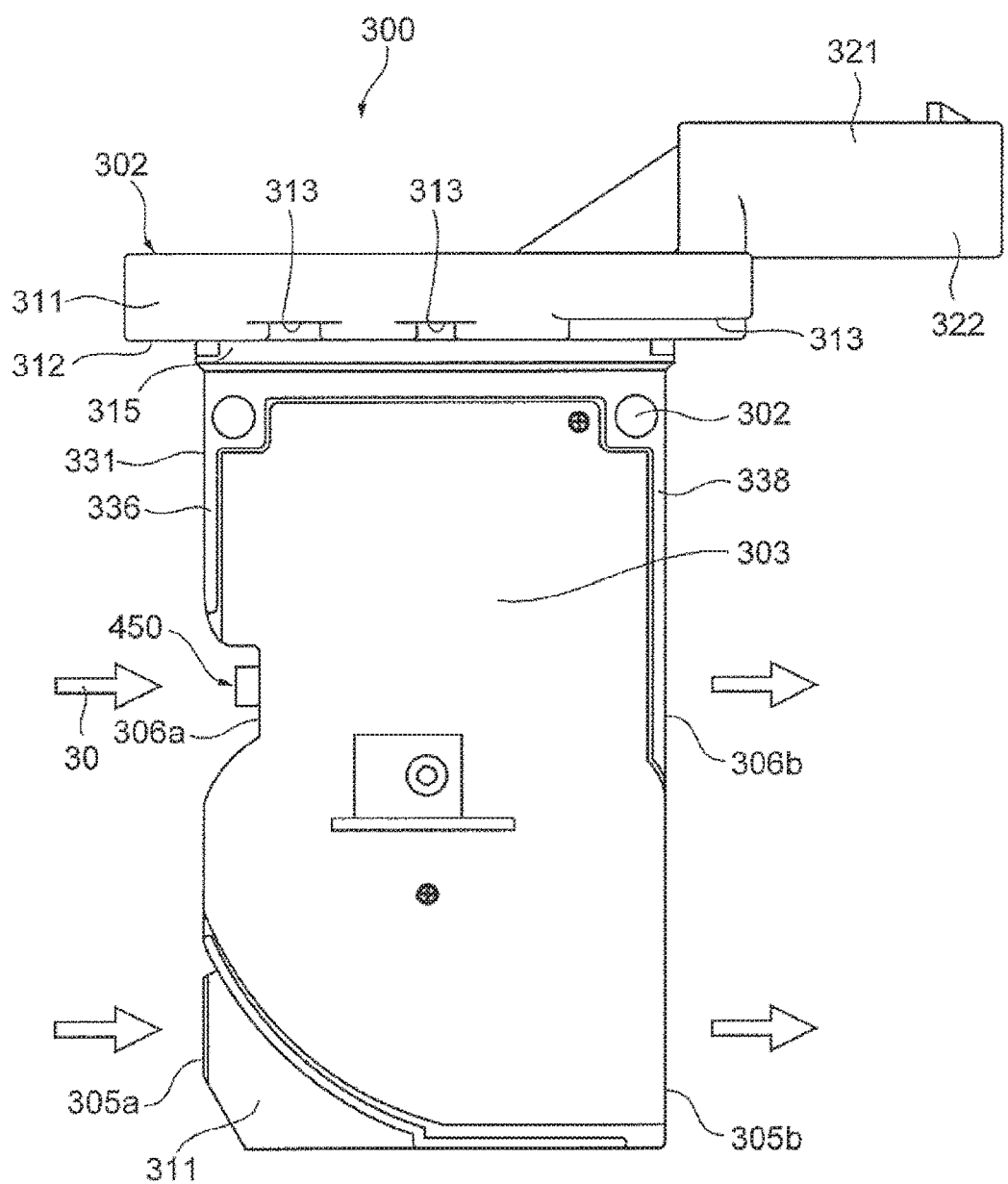
FIG. 2 is a front view of the physical quantity detection device.
Figure 3:
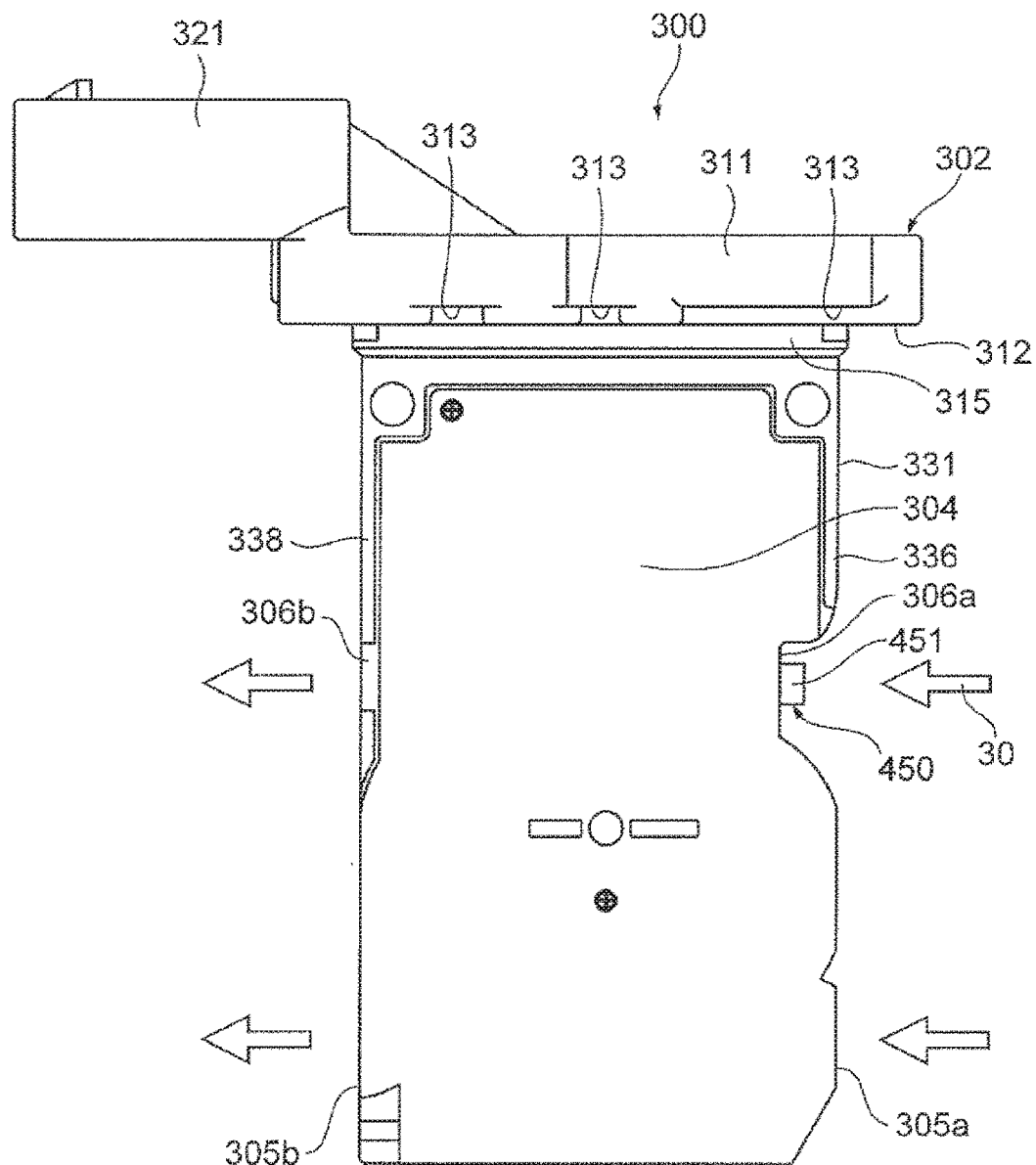
FIG. 3 is a rear view of the physical quantity detection device.
Figure 4:
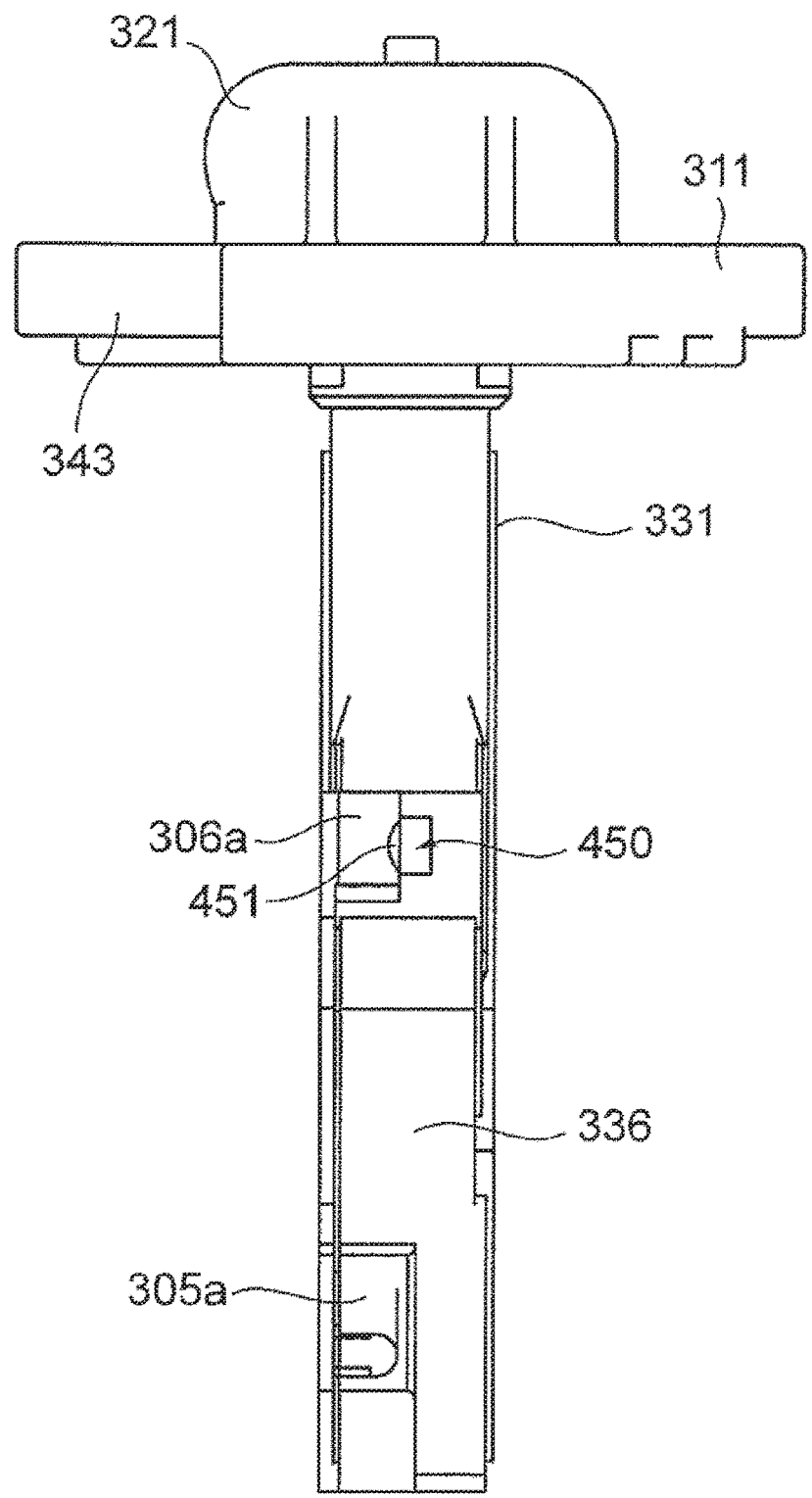
FIG. 4 is a left side view of the physical quantity detection device.
Figure 5:
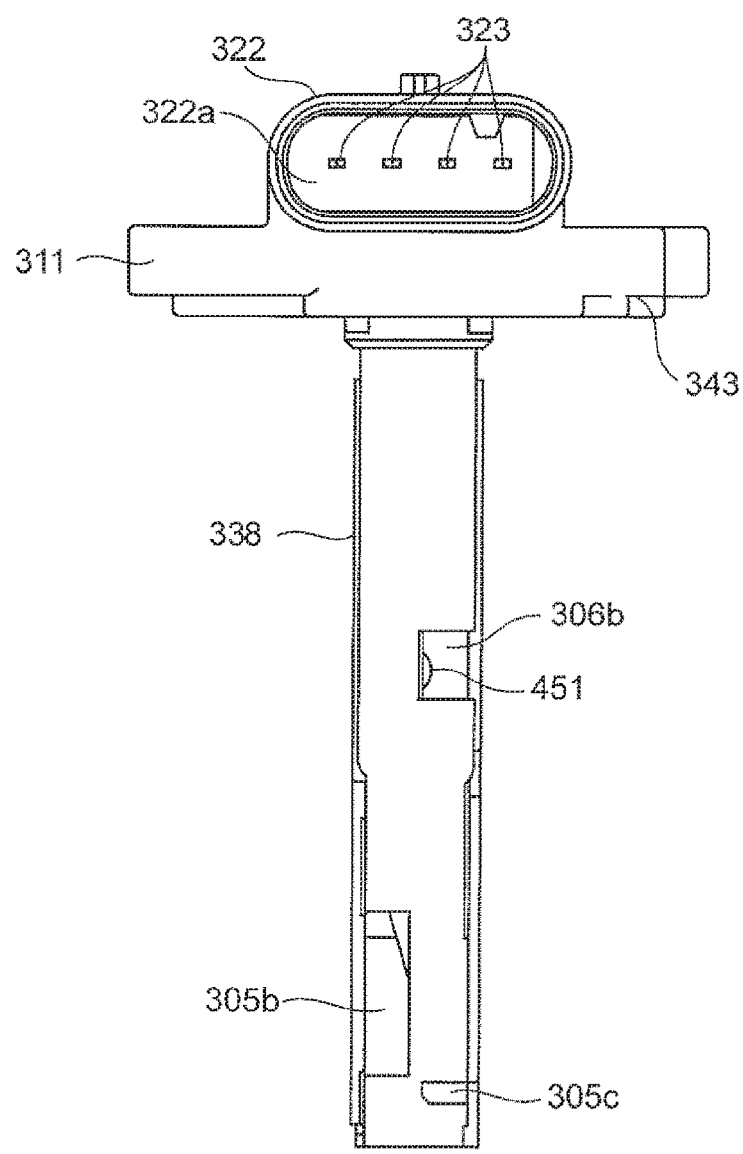
FIG. 5 is a right side view of the physical quantity detection device.
Figure 6:
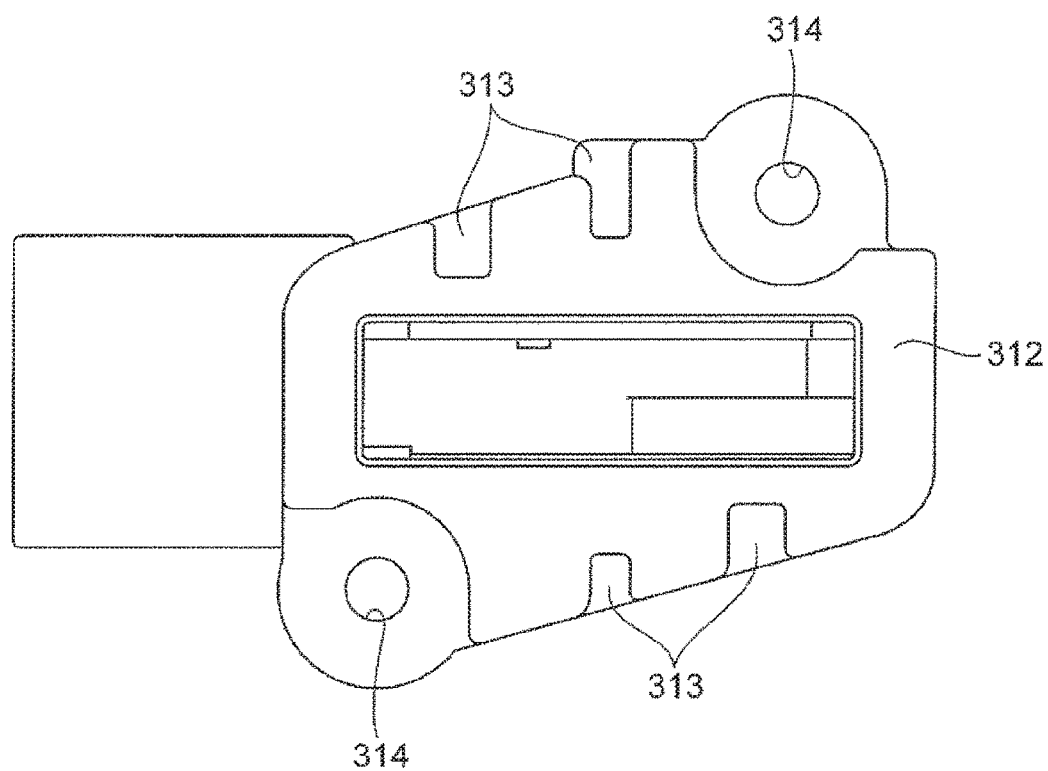
FIG. 6 is a bottom view of the physical quantity detection device.

FIGS. 2 to 6 are diagrams illustrating the exterior of the physical quantity detection device 300, in which FIG. 2 is a front view of the physical quantity detection device 300, FIG. 3 is a rear view, FIG. 4 is a left side view, FIG. 5 is a right side view, and FIG. 6 is a bottom view.

The physical quantity detection device 300 is provided with a housing 302, a front cover 303, and a rear cover 304 as components forming a casing part. The housing 302 includes a flange 311 for fixing the physical quantity detection device 300 to the intake body that is the main passage 124, an external connecting portion 321 equipped with a connector which protrudes outward from the flange 311 for electrical connection with an external machine, and a measurement unit 331 which is extended to protrude from the flange 311 to the center of the main passage 124.

Figure 7:
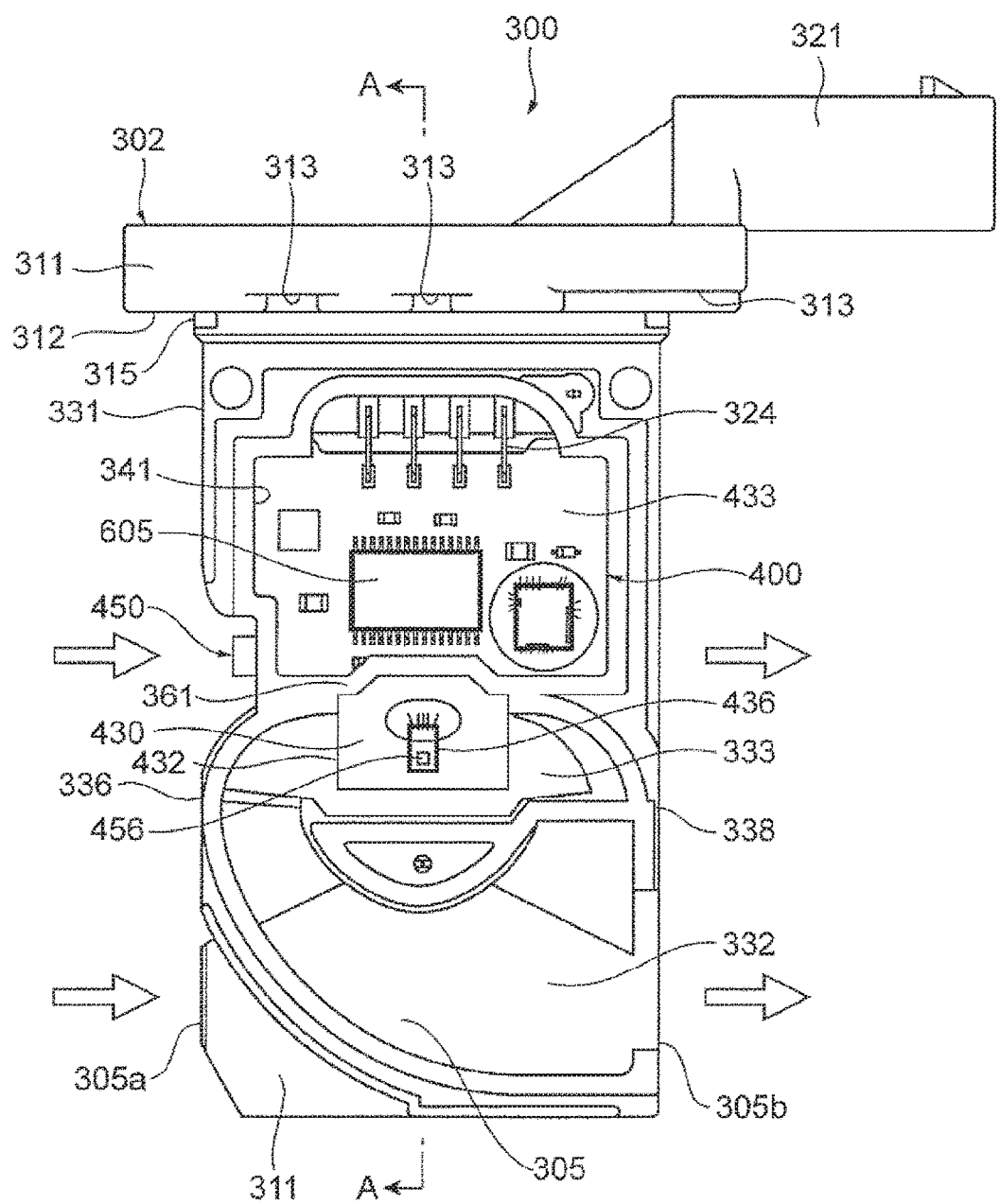
FIG. 7 is a front view illustrating a state where a front cover is removed from the physical quantity detection device.
Figure 8:
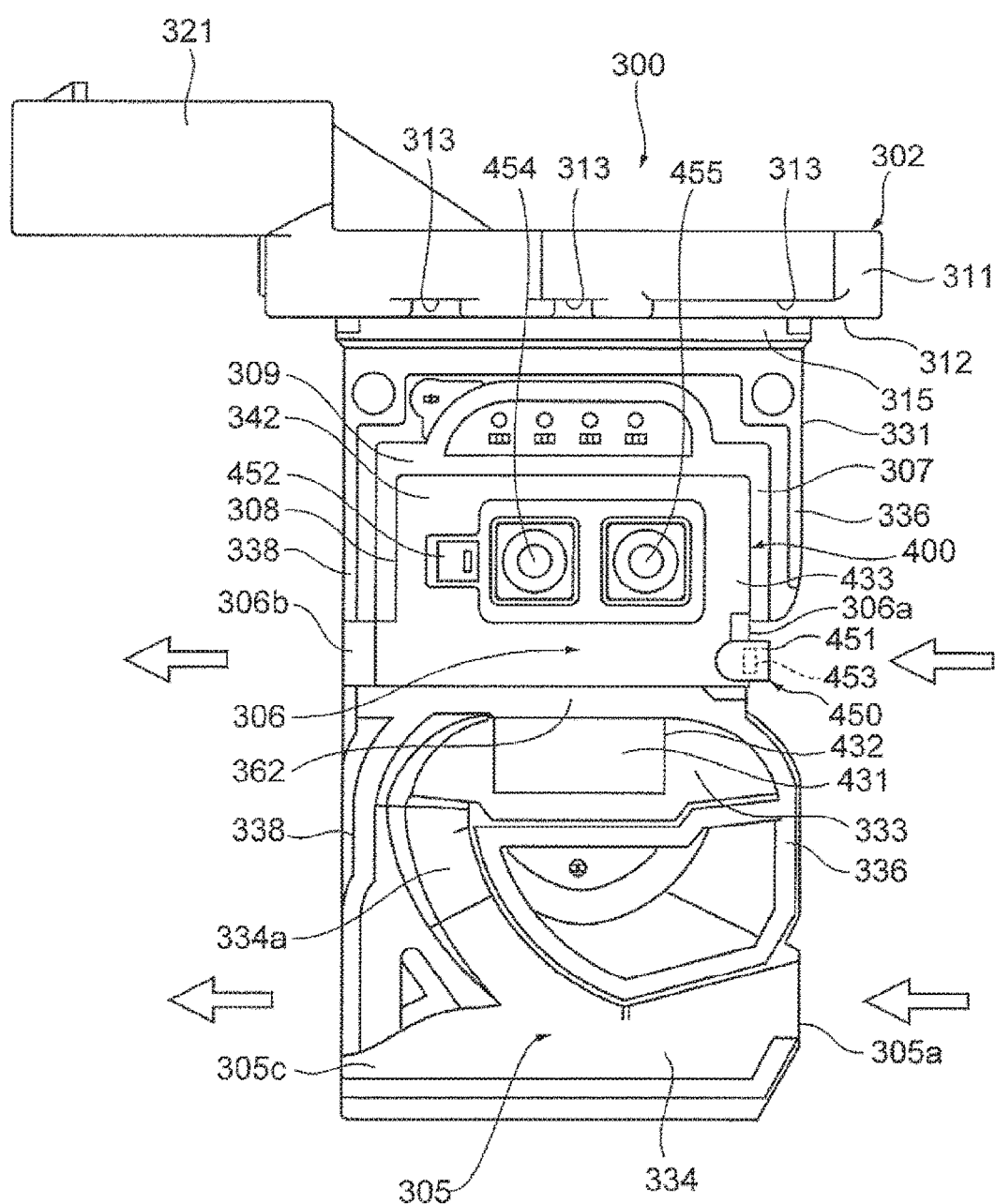
FIG. 8 is a rear view illustrating a state where a rear cover is removed from the physical quantity detection device.

The measurement unit 331 is inserted and integrally provided with a printed circuit board 400 (see FIGS. 7 and 8). The printed circuit board 400 includes a plurality of detection units for detecting various physical quantities of the measuring target gas 30 flowing in the main passage 124, and a circuit unit for processing signals detected by the plurality of detection units.

The measurement unit 331 is provided with bypass passage grooves in the front surface and the rear surface, and there are formed a first bypass passage 305 and a second bypass passage 306 in cooperation of the front cover 303 and the rear cover 304 (see FIG. 7 or 8). In the distal end portion of the measurement unit 331, there are provided a first bypass passage inlet 305a for taking part of the measuring target gas 30 such as the intake air into the first bypass passage 305, and a first bypass passage outlet 305b for returning the measuring target gas 30 from the first bypass passage 305 to the main passage 124.

In the intermediate portion of the measurement unit 331 near the flange 311 from the first bypass passage 305, there are provided a second bypass passage inlet 306a for taking part of the measuring target gas 30 such as the intake air into the second bypass passage 306, and a second bypass passage outlet 306b for returning the measuring target gas 30 from the second bypass passage 306 to the main passage 124. In the middle of the first bypass passage 305, a flow rate detection unit 456 (see FIG. 7) is provided to configure one of the detection units, and to detect the flow rate of the measuring target gas 30. The second bypass passage 306 includes a passage portion which connects the second bypass passage inlet and the second bypass passage outlet in a straight line shape, and a sensor chamber 342 which communicates with the passage portion and includes a detection sensor (see FIG. 8). In the sensor chamber 342, pressure sensors 454 and 455 and a temperature and humidity sensor 452 are contained as the detection unit to detect the physical quantities different from the flow rate provided in the rear surface of the printed circuit board 400.

2.2 Effects Based on Exterior Structure of Physical Quantity Detection Device 300

The physical quantity detection device 300 is provided with the second bypass passage inlet 306a an the middle of the measurement unit 331 which is extended from the flange 311 in a direction toward the center of the main passage 124, and the first bypass passage inlet 305a in the distal end portion of the measurement unit 331. Therefore, the gas near the center portion away from the internal wall surface can be taken into the first bypass passage 305 and the second bypass passage 306 instead of the vicinity of the internal wall surface of the main passage 124.

Therefore, the physical quantity detection device 300 can measure the physical quantity of the gas in a portion away from the internal wall surface of the main passage 124, and it is possible to suppress a reduction in measurement accuracy due to an influence such as heat. The vicinity of the internal wall surface of the main passage 124 is easily influenced by the temperature of the main passage 124, and comes to be in a state where the temperature of the measuring target gas 30 is different from the actual temperature of the gas, and thus becomes different from an average state of the main gas in the main passage 124. In particular, in a case where the main passage 124 is the intake body of the engine, the main passage is influenced by the heat from the engine, and kept in a high temperature in many cases. Therefore, the gas in the vicinity of the internal wall surface of the main passage 124 is highly heated with respect to the original air temperature of the main passage 124 in many cases, which causes the measurement accuracy to be lowered.

In the vicinity of the internal wail surface of the main passage 124, a fluid resistance is large, and the flow rate comes to be lowered compared to an average flow rate of the main passage 124. Therefore, when the gas in the vicinity of the internal wall surface of the main passage 124 is taken as the measuring target gas 30 into the first bypass passage 305 and the second bypass passage 306, there is a concern that the reduction in flow rate with respect to the average flow rate of the main passage 124 results in a measurement error of the physical quantity. Therefore, the first bypass passage 305 where the flow rate detection unit is disposed is provided with the first bypass passage inlet 305a in the distal end portion of the measurement unit 331 which is extended thin and long toward the center of the main passage 124 from the flange 311.

On the other hand, the second bypass passage 306 is provided with the second bypass passage inlet 306a in the intermediate portion of the measurement unit 331, and a humidity and pressure detection unit is disposed therein with which the physical quantity can be measured regardless of the reduction in flow rate in the vicinity of the internal wall surface. In addition, the first bypass passage 305 is provided with the first bypass passage outlet 305b in the distal end portion of the measurement unit 331, and provided with the second bypass passage outlet 306b in the intermediate portion of the measurement unit 331, both of which form the bypass passage independently from each other. Therefore, each detection unit can secure a necessary flow rate, and the measurement error can be reduced.

The measurement unit 331 is formed in a long shape extending along an axis toward the center from an outer wall of the main passage 124, and the thick width is formed in a narrow shape as illustrated in FIGS. 4 and 5. In other words, the measurement unit 331 of the physical quantity detection device 300 is formed such that the width of the side surface is thin and the front surface is in a substantially rectangular shape. With this configuration, the physical quantity detection device 300 can be provided with a sufficiently long bypass passage, and the fluid resistance against the measuring target gas 30 can be suppressed to a small value. Therefore, the physical quantity detection device 300 can measure the flow rate of the measuring target gas 30 with a high accuracy while suppressing the fluid resistance to a small value.

2.3 Structure of Temperature Detection Unit 451

A temperature detection unit 451 serves as one of the detection units for detecting the physical quantity of the measuring target gas 30 flowing in the main passage 124, and is provided in the printed circuit board 400. The printed circuit board 400 includes a protrusion portion 450 which protrudes toward the upstream of the measuring target gas 30 from the second bypass passage inlet 306a of the second bypass passage 306. The temperature detection unit 451 is provided in the protrusion portion 450 and also in the rear surface of the printed circuit board 400. The temperature detection unit 451 includes a chip type of temperature sensor 453. The temperature sensor 453 and the wiring portion thereof are coated with a synthetic resin material, and it is prevented electrolytic corrosion caused when saltwater is adhered. The synthetic resin material is applied onto the rear surface of the protrusion portion 450 in a melted state, and cured after application to cover the temperature sensor 453.

For example, as illustrated in FIG. 8, an upstream outer wall 336 in the measurement unit 331 of the housing 302 is recessed toward the downstream side in the center portion of the measurement unit 331 provided with the second bypass passage inlet 306a. The protrusion portion 450 of the printed circuit board 400 protrudes toward the upstream side from the recessed upstream outer wall 336. The distal end of the protrusion portion 450 is disposed at a position recessed from the surface on the most upstream side of the upstream outer wall 336. The temperature detection unit 451 is provided on the rear surface side of the printed circuit board 400 (that is, on a side near the second bypass passage 306) and the upstream side thereof.

Since the second bypass passage inlet 306a is formed continuously to the downstream side of the temperature detection unit 451, the measuring target gas 30 flowing from the second bypass passage inlet 306a into the second bypass passage 306 flows into the second bypass passage inlet 306a after coming in contact with the temperature detection unit 451, and the temperature is detected when coming in contact with the temperature detection unit 451. The measuring target gas 30 coming in contact with the temperature detection unit 451 flows in this state from the second bypass passage inlet 306a into the second bypass passage 306, and passes through the second bypass passage 306 so as to be discharged from the second bypass passage outlet 306b to the main passage 124.

2.4 Effects Related to Temperature Detection Unit 451

The temperature of the gas flowing from the upstream side in a direction along the flowing of the measuring target gas 30 into the second bypass passage inlet 306a is measured by the temperature detection unit 451. Furthermore, since the gas flows from the distal end portion of the protrusion portion 450 toward a proximal end portion, the temperature of the proximal end portion of the protrusion portion 450 is cooled down in a direction approaching to the temperature of the measuring target gas 30. The temperature of the intake pipe (the main passage 124) is normally increased, and the heat is transferred to the proximal end portion of the protrusion portion 450 through the upstream outer wall 336 or the printed circuit board 400 in the measurement unit 331 from the flange 311 or an abutting portion 315, and thus there is a concern that the accuracy of the temperature measurement of the temperature detection unit 451 is influenced. As described above, after the measuring target gas 30 is measured by the temperature detection unit 451, the proximal end portion is cooled down when the gas flows to the proximal end portion of the protrusion portion 450. Therefore, it is possible to suppress the heat from being transferred from the flange 311 or the abutting portion 315 to the proximal end portion of the protrusion portion 450 through the upstream outer wall 336 or the printed circuit board 400 in the measurement unit 310.

In particular, since the upstream outer wall 336 in the measurement unit 331 is formed in a recess shape (see FIGS. 7 and 8) toward the downstream side in the proximal end portion of the protrusion portion 450, the length of the upstream outer wall 336 from the flange 311 up to the proximal end portion of the protrusion portion 450 can be made long, a heat conduction distance from the flange 311 and the abutting portion 315 can be made long, and a distance of the portion cooled down by the measuring target gas 30 can be made long. Therefore, it is possible to reduce the influence of heat caused from the flange 311 or the abutting portion 315. In addition, for example, when the measurement unit 331 is inserted from a mounting hole provided in the main passage 124 to the inside, the protrusion portion 450 does not hinder an operation of mounting the physical quantity detection device 300 in the main passage 124. The protrusion portion 450 can be prevented from coming in conflict with the main passage 124, and thus protected from damage.

2.5 Structure and Effects of Flange 311

In the flange 311, a plurality of recesses 313 are provided in a lower surface 312 facing the main passage 124 to reduce a heat transfer surface with respect to the main passage 124, so that the physical quantity detection device 300 is hardly influenced by the heat. The physical quantity detection device 300 is configured such that the measurement unit 331 is inserted to the inside from a mounting hole provided in the main passage 124, and the lower surface 312 of the flange 311 faces the main passage 124. The main passage 124 is the intake body for example. The main passage 124 is normally kept at a high temperature. On the contrary, upon activating in a cold region, it is considered that the main passage 124 is at an extremely low temperature. When such a high or low temperature of the main passage 124 has an influence on the temperature detection unit 451 or the flow rate measurement described below, the measurement accuracy is lowered. The flange 311 includes the recess 313 in the lower surface 312 to form a space between the lower surface 312 facing the main passage 124 and the main passage 124. Therefore, the heat transfer from the main passage 124 to the physical quantity detection device 300 is reduced, and a reduction in measurement accuracy caused by the heat can be prevented.

Since screw holes 314 of the flange 311 are used to fix the physical quantity detection device 300 to the main passage 124, the space between the surface facing the main passage 124 surrounding the respective screw holes 314 and the main passage 124 is formed to separate the surface facing the main passage 124 surrounding these screw holes 314 from the main passage 124. With such a configuration, the heat transfer from the main passage 124 with respect to the physical quantity detection device 300 is reduced, and the structure is made to enable to prevent the reduction in measurement accuracy due to the heat.

Furthermore, the recess 313 operates to reduce an influence of shrinkage of the resin of the flange 311 at the time of forming the housing 302 not only the reduction effect of the heat transfer. The flange 311 is formed with a thick resin compared to the measurement unit 331. At the time when the housing 302 is molded with resin, a volume is shrunk when the resin is cooled down from a high temperature to a low temperature and cured, and a distortion may occur due to stress. The volume shrinkage can be evenly made by forming the recess 313 in the flange 311, and a stress concentration can be reduced.

The measurement unit 331 is inserted to the inside from the mounting hole provided in the main passage 124, and fixed to the main passage 124 by being screwed through the flange 311 of the physical quantity detection device 300. The physical quantity detection device 300 is desirably fixed in a predetermined positional relation to the mounting hole provided in the main passage 124. The recess 313 provided in the flange 311 can be used for positioning the main passage 124 and the physical quantity detection device 300. A projection may be formed in the main passage 124 to form a shape such that the projection is fitted to the recess 313, and the physical quantity detection device 300 can be fixed to the main passage 124 at an accurate position.

2.6 Structure of External Connecting Portion 321

The external connecting portion 321 includes a connector 322 which is provided in the upper surface of the flange 311 and protrudes from the flange 311 toward the downstream side in a flowing direction of the measuring target gas 30. In the connector 322, there is provided a plug-in hole 322a for plugging a communication cable which is connected to the control device 200. Four external terminals 323 are provided in the plug-in hole 322a as illustrated in FIG. 5. The external terminal 323 serves as a terminal for outputting information of the physical quantity (measurement result) of the physical quantity detection device 300 and a power terminal for supplying a direct current power to operate the physical quantity detection device 300. Further, the connector 322 in this embodiment has been described about a case where the connector protrudes from the flange 311 toward the downstream side in the flowing direction of the measuring target gas 30, and has an insertion shape from the downstream side in the flowing direction toward the upstream side, but the invention is not limited to this shape. For example, the connector may vertically protrude from the upper surface of the flange 311 and have an insertion shape along the extending direction of the measurement unit 331, and may be changed in various forms.

3. Entire Structure and Effects of Housing 302

3.1 Structures and Effects of Bypass Passage and Flow Rate Detection Unit

Figure 9:
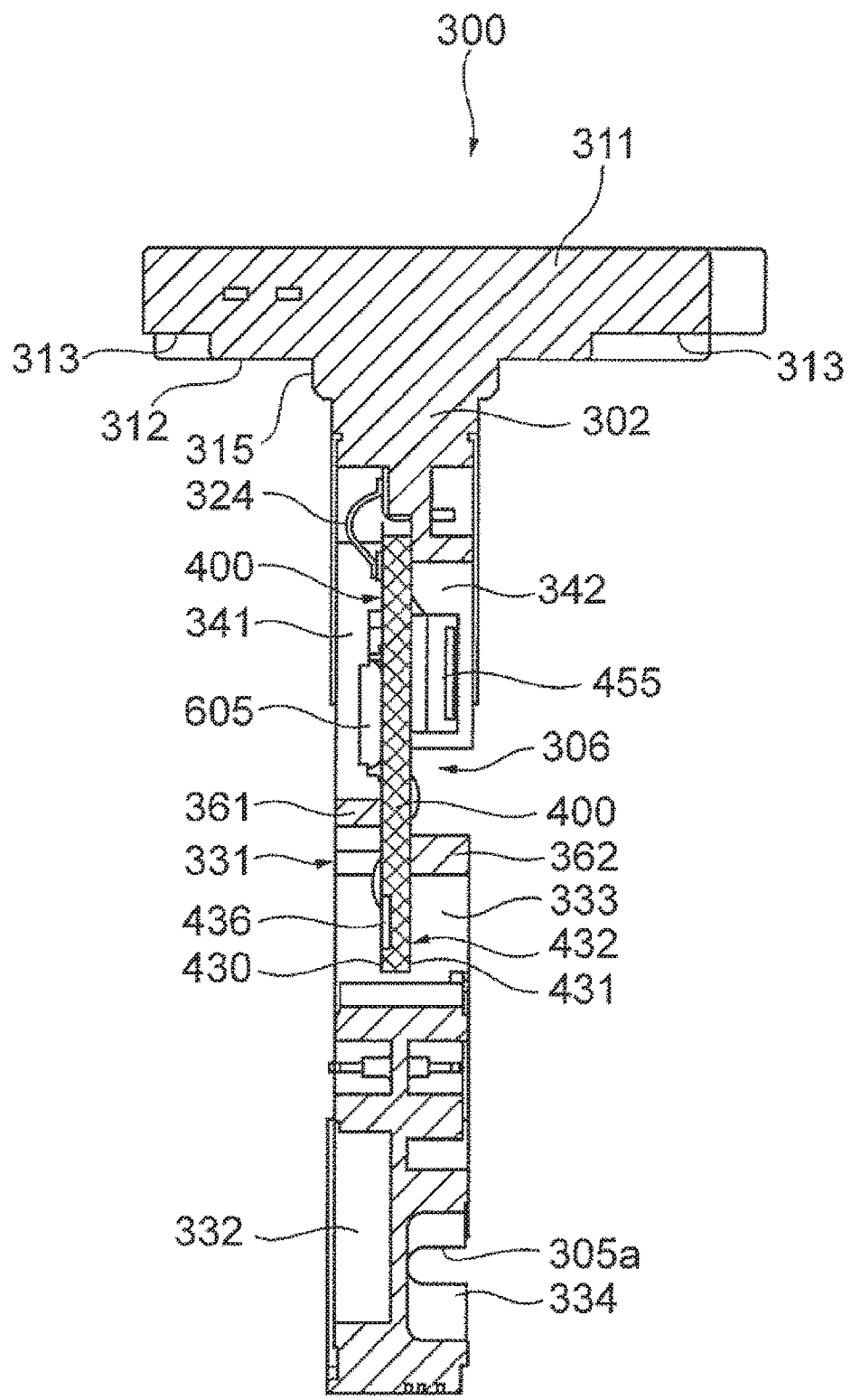
FIG. 9 is a cross-sectional view taken along arrow A-A of FIG. 7.
Figure 10A:
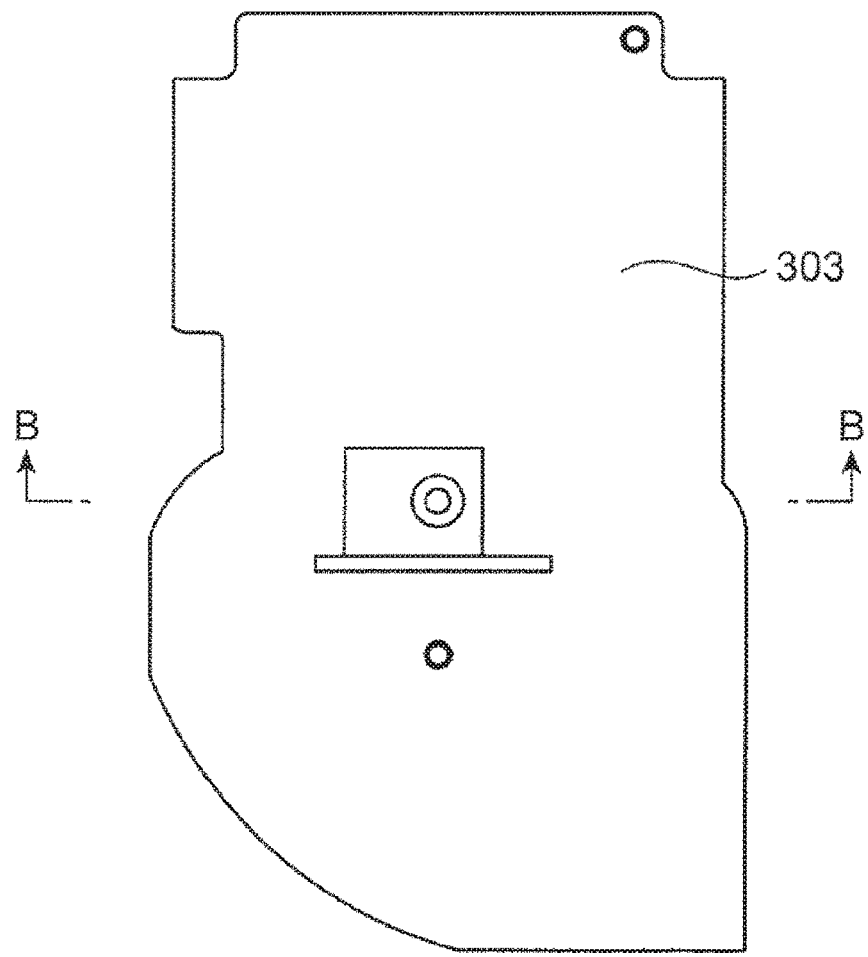
FIGS. 10A and 10B are diagrams for describing a configuration of the front cover.
Figure 10B:
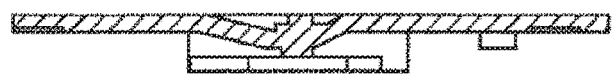

FIGS. 7 and 9 illustrate a state of the housing 302 where the front cover 303 and the rear cover 304 are removed from the physical quantity detection device 300. FIG. 7 is a front view of the housing 302, FIG. 8 is a rear view of the housing 302, and FIG. 9 is a cross-sectional view taken along a line A-A of FIG. 7.

The housing 302 is structured such that the measurement unit 331 is extended from the flange 311 toward the center of the main passage 124, the printed circuit board 400 is disposed on the proximal end side of the measurement unit 331, and the bypass passage groove for forming the first bypass passage 305 is provided on the distal end side of the measurement unit 331.

The printed circuit board 400 has a flat plate shape and includes a main body portion 433 which partitions the proximal end portion of the measurement unit 331 into the front surface side and the rear surface side and has a substantially rectangular shape in plan view, and a protrusion portion 432 which is disposed in the first bypass passage 305 to protrude from one side of the main body portion 433.

The printed circuit board 400 is provided along the plan of the measurement unit 331 as illustrated in FIGS. 7 and 8, and disposed in parallel along the surface of the measurement unit 331 to partition the proximal end portion of the measurement unit 331 into the front surface side and the rear surface side at the intermediate position between the front surface and the rear surface of the measurement unit 331 as illustrated in FIG. 9.

In the printed circuit board 400, the flow rate detection unit (air flow rate sensor) 456 is disposed in the same front surface (one surface) as the mounting surface where a circuit such as a microprocessor is mounted, and at least one or more physical quantity detection sensors (for example, a humidity sensor, a pressure sensor, etc.) are disposed in the rear surface (other surface). In other words, the printed circuit board 400 includes, in its front surface, a detection sensor surface region in which the flow rate detection unit (the physical quantity detection sensor) 456 is disposed, and a circuit component surface region in which the circuit component such as an LSI other than the physical quantity detection sensor is disposed. Then, a facing surface region facing the circuit component surface region is provided in the rear surface of the printed circuit board 400, and at least a part of the facing surface region is exposed to the second bypass passage 306 in the rear surface of the printed circuit board.

In this embodiment, the circuit component is disposed in the front surface of the printed circuit board 400 to be wire-bonded to the LSI or the air flow rate sensor, and the circuit component is disposed in the rear surface of the printed circuit board 400 to be soldered to the temperature and humidity sensor 452 or the pressure sensors 454 and 455. In this way, the printed circuit board 400 can be easily manufactured by disposing the wire-bonding circuit component in one surface of the printed circuit board 400.

A circuit chamber 341 is formed on the front surface side of the measurement unit 331 to contain the circuit component such as the LSI and the microprocessor mounted in the front surface of the printed circuit board 400. The circuit chamber 341 is sealed in cooperation with the front cover 303, and completely isolated from the outside.

Then, the second bypass passage 306 is formed on the rear surface side by the printed circuit board 400. The second bypass passage 306 is formed in cooperation with the rear cover 304. The second bypass passage 306 includes the passage portion which is extended in a straight line along a flowing direction of the measuring target gas 30 flowing in the main passage 124, and the sensor chamber 342 which is formed at a position shifted to a direction orthogonal or perpendicular to the flowing direction of the measuring target gas 30 from the passage portion. The sensor chamber 342 is formed in a predetermined interior space in which the rear surface side is sealed by the rear cover 304, but communicates to the outside through the second bypass passage 306 which is continuously formed on the distal end side of the measurement unit 331. In the sensor chamber 342, the pressure sensors 454 and 455 and the temperature and humidity sensor 452 mounted in the rear surface of the printed circuit board 400 are contained.

The bypass passage groove for forming the first bypass passage 305 includes a front-side bypass passage groove 332 illustrated in FIG. 7, and a rear-side bypass passage groove 334 illustrated in FIG. 8. The front-side bypass passage groove 332 is gradually bent toward the flange 311 (on the proximal end side of the measurement unit 331) as it goes from the first bypass passage outlet 305b opened to a downstream external wall 338 of the measurement unit 331 toward the upstream outer wall 336, and communicates with an opening 333 at a position near the upstream outer wall 336. The opening 333 is formed to pass through the measurement unit 331 in a thickness direction. The opening 333 is formed along the flowing direction of the measuring target gas 30 of the main passage 124 to be extended along between the upstream outer wall 336 and the downstream external wall 338.

In the opening 333, the protrusion portion 432 which is a part of the printed circuit board 400 is disposed. The protrusion portion 432 of the printed circuit board 400 passes through partition walls 361 and 362 which separate the circuit chamber 341 of the measurement unit 331 and the second bypass passage 306 to protrude to the opening 333.

The protrusion portion 432 includes a measurement flow-passage surface 430 and a rear surface 431 thereof which are extended in parallel along the flowing direction of the measuring target gas 30 in the opening 333.

The rear-side bypass passage groove 334 moves from the first bypass passage inlet 305a opened to the upstream outer wall 336 of the measurement unit 331 toward the downstream external wall 338, and branches off into two parts at an intermediate position between the upstream outer wall 336 and the downstream external wall 338. One of the branches is extended itself in a straight line shape as a discharge passage to communicate with a discharge port 305c opened to the downstream external wall 338. The other one of the branches is gradually bent toward the flange 311 (the proximal end side of the measurement unit 331) as it goes to the downstream external wall 338, and communicates with the opening 333 at a position near the downstream external wall 338.

The rear-side bypass passage groove 334 forms an inlet groove of the first bypass passage 305 through which the measuring target gas 30 flows in from the main passage 124. The front-side bypass passage groove 332 forms an outlet groove of the first bypass passage 305 through which the measuring target gas 30 taken in from the rear-side bypass passage groove 334 returns to the main passage 124. The front-side bypass passage groove 332 and the rear-side bypass passage groove 334 are provided on the distal end side of the measurement unit 331. Therefore, the gas in a portion separated from the internal wall of the main passage 124 (that is, the gas flowing a portion near the center portion of the main passage 124) can be taken in as the measuring target gas 30. The gas flowing in the vicinity of the internal wall of the main passage 124 is influenced by the temperature of the wall surface of the main passage 124, and has a temperature different from an average temperature of the gas flowing in the main passage 124 such as the measuring target gas 30 in many cases. In addition, the gas flowing in the vicinity of the internal wall surface of the main passage 124 shows a flow speed delayed from an average flow speed of the gas flowing in the main passage 124 in many cases. Since the physical quantity detection device 300 according to the embodiment hardly receives such an influence, it is possible to suppress a reduction in measurement accuracy.

In the embodiment, the bypass passage grooves 332 and 334 are provided to form the first bypass passage 305 in the housing 302, the first bypass passage 305 is completely configured by the bypass passage grooves 332 and 334 and by the covers 303 and 304 by putting the covers 303 and 304 on the front surface and the rear surface of the housing 302. With such a structure, it is possible to form all the bypass passage grooves as a part of the housing 302 in a resin mold process of the housing 302. In addition, since molds are provided on both surfaces of the housing 302 at the time of forming the housing 302, it is possible to form both of the from side bypass passage groove 332 and the rear-side bypass passage groove 334 as a part of the housing 302 by using the molds of the both sides. The bypass passages of the both surfaces of the housing 302 can be completely formed providing the front cover 303 and the rear cover 304 in the both surfaces of the housing 302. Since the front-side bypass passage groove 332 and the rear-side bypass passage groove 334 are formed in the both surfaces of the housing 302 using the mold, the first bypass passage 305 can be formed with a high accuracy. In addition, a high productivity can be achieved.

As illustrated in. FIG. 8, a part of the measuring target gas 30 flowing in the main passage 124 is taken into the rear-side bypass passage groove 334 from the first bypass passage inlet 305a, and flows in the rear-side bypass passage groove 334. Then, a foreign object having a heavy mass in the measuring target gas 30 flows to the discharge passage extending in a straight line from the branch together with a part of the measuring target gas 30, and is discharged from the discharge port 305c of the downstream external wall 338 to the main passage 124.

The rear-side bypass passage groove 334 has a shape deepening as it progresses. The measuring target gas 30 gradually moves to the front side of the measurement unit 331 as it goes along the rear-side bypass passage groove 334. In particular, the rear-side bypass passage groove 334 is provided with a steep slope portion 334a which is steeply deepened before the opening 333. Part of the air having a light mass moves along the steep slope portion 334a, and flows toward the measurement flow-passage surface 430 of the printed circuit board 400 in the opening 333. On the other hand, since it is not easy for the foreign object having a heavy mass to abruptly change its route, the foreign object flows toward a measurement flow-passage rear surface 431.

As illustrated in FIG. 7, the measuring target gas 30 moved toward the surface side in the opening 333 flows along the measurement flow-passage surface 430 of the printed circuit board while performing the heat transfer with respect to the flow rate detection unit 456 to measure the flow rate through a heat transfer surface exposing portion 436 provided in the measurement flow-passage surface 430, and the flow rate is measured. The air flowed from the opening 333 to the front-side bypass passage groove 332 flows also along the front-side bypass passage groove 332, and discharged from the first bypass passage outlet 305b opened to the downstream external wall 338 toward the main passage 124.

Since a material having a heavy mass such as dust mixed in the measuring target gas 30 has large inertia, it is difficult to steeply change to the depth direction of the groove along the front surface of a portion of the steep slope portion 334a where the depth of the groove is steeply deepened along. Therefore, the foreign object having a heavy mass moves toward the measurement flow-passage rear surface 431, and thus it is suppressed that the foreign object approaches the heat transfer surface exposing portion 436. In this embodiment, a majority of foreign objects having a heavy mass other than the gas passes through the measurement flow-passage rear surface 431 (rear surface) of the measurement flow-passage surface 430. Therefore, it is possible to reduce an influence of contamination due to the foreign objects such as oil, carbon, or dust, and the reduction in measurement accuracy can be suppressed. In other words, since the shape is formed such that the route of the measuring target gas 30 is abruptly changed along an axis traversing the flowing axis of the main passage 124, the influence of the foreign object mixed in the measuring target gas 30 can be reduced.

In this embodiment, the flow passage formed by the rear-side bypass passage groove 334 faces the flange 311 from the distal end portion of the housing 302 while drawing a curve, the gas flowing the bypass passage at the position nearest to the flange 311 flows in an opposite direction with respect to the flow in the main passage 124, and the bypass passage on the rear surface side (one side) is connected to the bypass formed on the front surface side (the other side) in a portion of the flow of the opposite direction. With such a configuration, the printed circuit board 400 can be easily fixed to the bypass passage of the heat transfer surface exposing portion 436. Furthermore, the measuring target gas 30 can be easily taken in at a position near the center portion of the main passage 124.

3.2 Structures and Effects of Second Bypass Passage and Humidity and Pressure Detection Unit The second bypass passage 306 is configured in cooperation with the housing 302, the printed circuit board 400 illustrated in FIGS. 8 and 9, and the rear cover 304 bonded to the housing 302. The printed circuit board 400 is provided along the surface of the measurement unit 331, and is disposed in parallel along the surface of the measurement unit 331 to partition the proximal end portion of the measurement unit 331 into the front surface side and the rear surface side at the intermediate position between the front surface and the rear surface of the measurement unit 331.

On the upstream side of the housing 302, there is provided a partition 307 which forms a part of the second bypass passage inlet 306a, is extended toward the flange 311 (the proximal end side of the measurement unit. 331), and blocks the measuring target gas 30 as illustrated in FIG. 8. Similarly, as illustrated in FIG. 8, on the downstream side of the housing 302, there is provided a partition 308 which forms a part of the second bypass passage outlet 306b, and is extended toward the flange 311 (the proximal end side of the measurement unit 331). In addition, the partitions 307 and 308 on the upstream and downstream side of the housing are connected by a partition 309 which is extended in a direction in parallel with the flow of the measuring target gas 30 to surround the temperature and humidity sensor 452 and the pressure sensors 454 and 455 in the intermediate portion connected to the flange 311. The partitions 307, 308, and 309 have the same height in the thickness direction of the measurement unit 331, and form the sensor chamber 342 by mounting the rear cover 304.

The second bypass passage 306 is extended in parallel with the flowing direction of the measuring target gas 30 flowing in the main passage 124, and the temperature and humidity sensor 452 and the pressure sensors 454 and 455 (the physical quantity detection sensors) are disposed at positions separated in a direction intersecting with a straight line connecting the second bypass passage inlet 306a and the second bypass passage outlet 306b. The inlet 306a and the outlet 306b of the second bypass passage 306 are vertically opened with respect to the measuring target gas 30 flowing in the main passage 124, and disposed on the same straight line in parallel with the flowing direction of the measuring target gas 30. In addition, the temperature and humidity sensor 452 and the pressure sensors 454 and 455 are disposed in the sensor chamber 342 surrounded by the partitions 307, 308, and 309 at positions shifted toward the flange 311 from a flowing line of the air in the passage portion connecting the second bypass passage inlet 306a and the second bypass passage outlet 306b.

In general, in a case where a plurality of sensors are configured by the same electronic circuit, the power consumption is simply increased according to the number of physical quantity detection sensors. It has been known that the power consumption (electric energy) is converted into heat (energy) through a resistor, the heating of the entire circuit is increased as the power consumption is increased. When the circuit is increased in its self-heating, the durability of the circuit component or the performance of the physical quantity detection sensor are adversely affected. A temperature range required for an automobile component becomes a wide range of −40° C. to 125° C. In particular, a semiconductor component such as a microprocessor is used in the electronic circuit of the physical quantity detection sensor. The semiconductor component is typically used in a range not exceeding a junction temperature of about 150° C. in accordance with a high humidity environment and the self-heating of the circuit. The junction temperature is a temperature of the junction portion between a semiconductor element and a lead line. When being used under an environment equal to or more than about 150° C., a durable life of the product is significantly lowered. Therefore, a radiation design is required to extremely suppress the self-heating of the circuit. In addition, from a viewpoint of the performance of the physical quantity detection device 100, there is a concern that the temperature increase due to the heat transfer caused by the self-heating of the circuit results in deterioration of the measurement accuracy of the detection sensor since a change in properties due to a temperature influence always occurs at high and low temperatures.

With regard to such a problem, the rear surface of the printed circuit board 400 in this embodiment forms a part of the second bypass passage 306. Therefore, the rear surface of the printed circuit board 400 is exposed to the air flowing in the second bypass passage 306. In other words, the self-heating occurring in the circuit component such as a microprocessor 605 mounted in the front surface of the printed circuit board 400 causes the heat transfer to the rear surface of the printed circuit board 400. Furthermore, the heating of the entire printed circuit board 400 can be suppressed by transferring the heat to the air flowing in the second bypass passage 306.

In addition, since the pressure sensor 455 is disposed at the back of the partition 307 on the upstream side of the housing 302, the measuring target gas 30 flowed to the second bypass passage 306 is prevented from coming into direct conflict with the pressure sensor 455, and it is possible to suppress the air flow from directly influencing on the pressure sensor 455. In other words, a dynamic pressure generated by the air flow is not detected by the pressure sensor 455 but can correctly measure a static pressure to be measured, so that the measurement accuracy can be secured.

The inlet 306a and the outlet 306b of the second bypass passage are positioned on the same line, and the detection sensor (herein, an order of disposing the plurality of detection sensors is not limited to that illustrated in FIG. 8) is shifted from the same line to be disposed in the intermediate portion of the partitions 307 and 308 on the upstream and the downstream sides of the housing 302. Therefore, it is possible to suppress dust and water droplets mixed into the measuring target gas 30 from coming into direct conflict with the detection sensor. Further, staining/deterioration and variation of the output can be reduced.

3.3 Structures and Effects of Rear Cover, and Humidity and Pressure Detection Unit FIGS. 10(a) and 10(b) and FIGS. 11(a) and 11(b) are diagrams illustrating configurations of the front cover and the rear cover. In addition, FIGS. 12(a) to 14(b) illustrate a plurality of embodiments of the second bypass passage configured by the rear cover.

As described above, the bypass passage groove is configured in the rear surface of the housing 302 to form the second bypass passage 306, and the rear cover 304 is disposed to separate the measuring target gas 30 from parts other than the inlet 306a and the outlet 306b of the second bypass passage of the bypass passage groove.

Figure 11A:
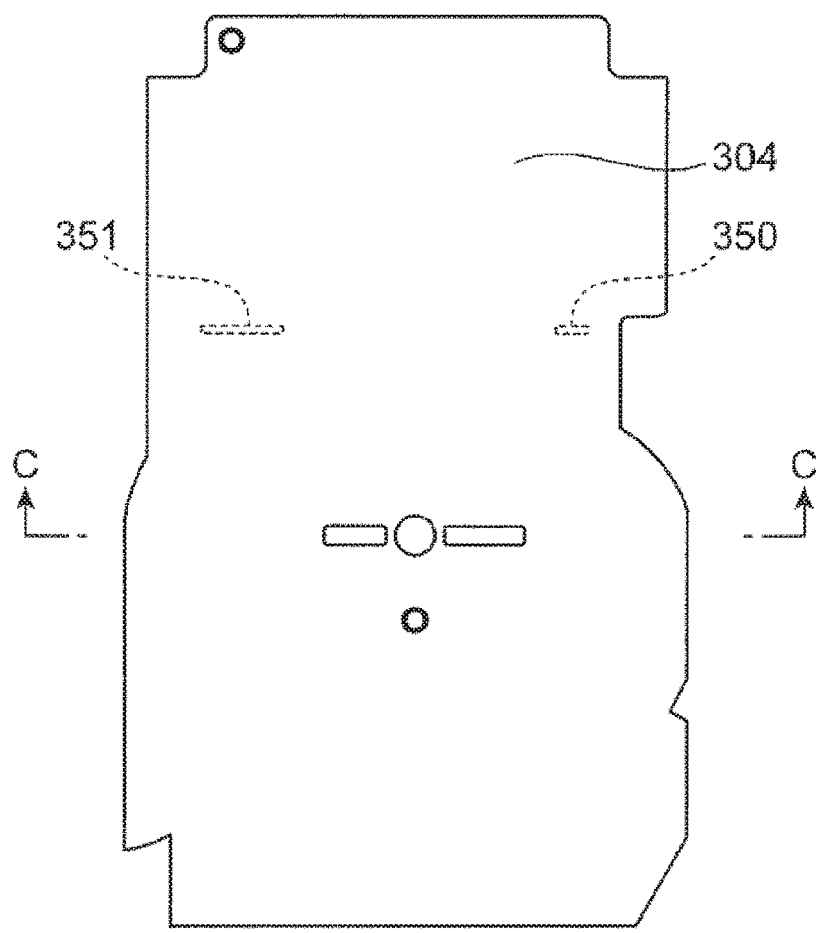
FIGS. 11A and 11B are diagrams for describing a configuration of the rear cover.
Figure 11B:
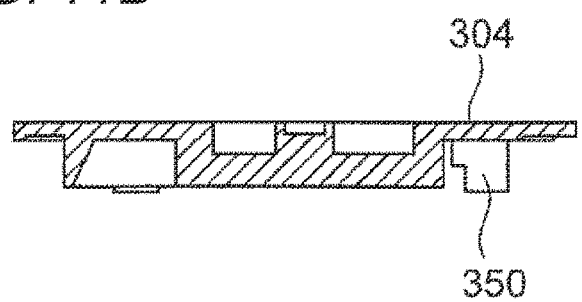
Figure 12B:
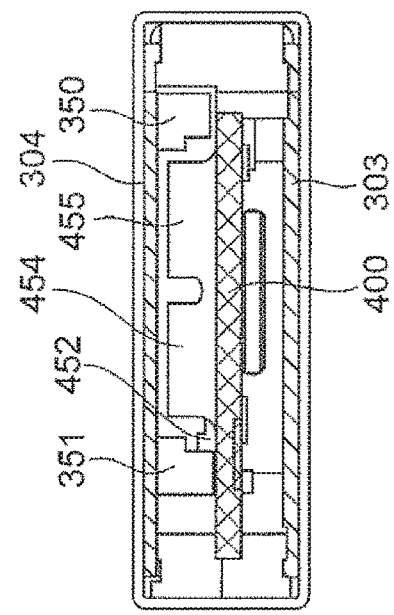
Figure 12A:
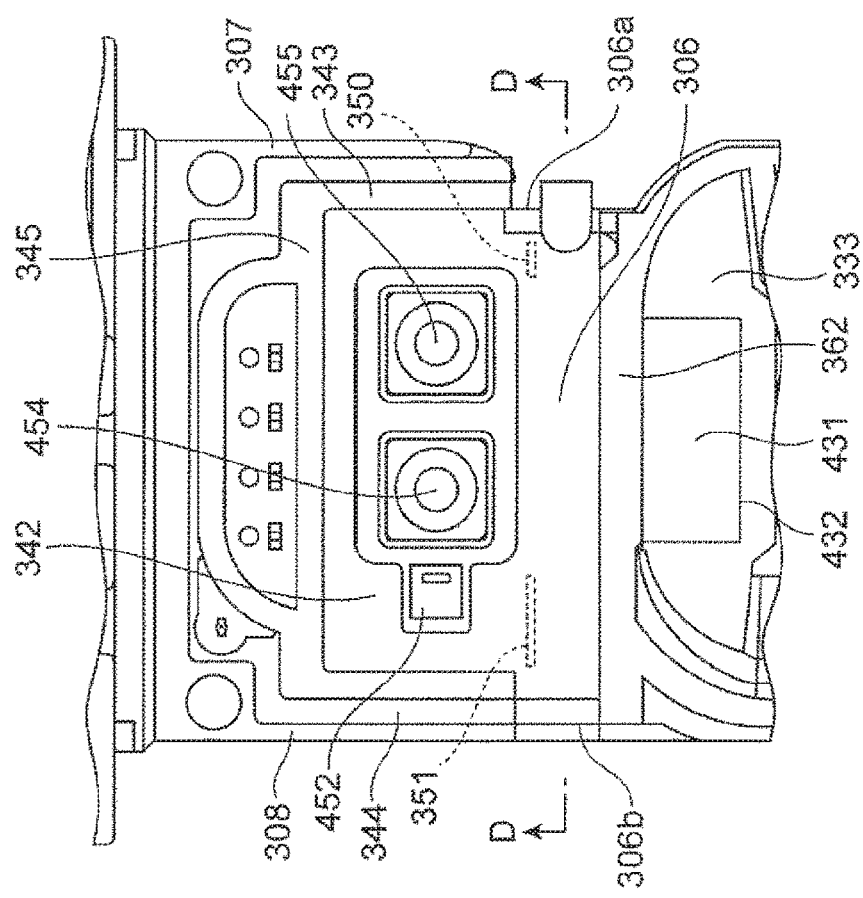

FIGS. 12(a) and 12(b) illustrate an example in which the temperature and humidity sensor 452 and the pressure sensors 454 and 455 are mounted in the rear surface of the printed circuit board 400. In FIGS. 11(a) and 12(a), a projection 350 on the upstream side formed in the rear cover 304 and a projection 351 on the downstream side are illustrated with a dotted line. FIG. 12(b) illustrates a cross section taken along a line D-D of FIG. 12(a), and shows an example of disposing the projections 350 and 351.

The projections 350 and 351 form a partition wall which partitions the second bypass passage 306 of the printed circuit board 400 into the passage portion and the sensor chamber 342 by mounting the rear cover 304. The projection 350 on the upstream side is formed to be extended along the flowing direction of the measuring target gas 30 along between the second bypass passage inlet 306a and the pressure sensor 455 on the upstream side. Then, the projection 351 on the downstream side is formed to be extended along the flowing direction of the measuring target gas 30 along between the pressure sensor 454 on the downstream side and the second bypass passage outlet 306b. The projections 350 and 351 both are formed integrally to the rear cover 304 by a thin protruding piece, protrude toward the printed circuit board 400 along the thickness direction of the measurement unit 331, and are disposed on a straight line at the same height position with respect to the longitudinal direction of the measurement unit 331 in parallel with the flowing of the measuring target gas 30.

In this embodiment, when the measuring target gas 30 flows in through the second bypass passage inlet 306a, the flowing is corrected by the projections 350 and 351 on the upstream and downstream sides, and passes through a straight line connecting the second bypass inlet 306a and the outlet 306b and then discharged to the outside from the outlet 306b.

In other words, since the sensor chamber 342 is shifted to the proximal end side of the measurement, unit 331 (on a side near the flange 311) from the passage portion of the second bypass passage 306, the measuring target gas 30 flowed from the second bypass passage inlet 306a into the second bypass passage 306 directly progresses through the passage portion of the second bypass passage 306, and then discharged to the outside from the second bypass passage outlet 306b, but not directly flows into the sensor chamber 342. Therefore, it is possible to suppress the measuring target gas 30 from coming into direct conflict with the physical quantity detection sensor such as the pressure sensors 454 and 455 an the sensor chamber 342 and the temperature and humidity sensor 452.

In general, a water droplet or a pollutant having a certain mass in the intake pipe is mixed to the measuring target gas 30 and passes through the second bypass passage 306. Therefore, the measuring target gas 30 is suppressed from coming into direct conflict with the physical quantity detection sensor. Therefore, the staining and deterioration of the physical quantity detection sensor or the output variation due to the water droplet can be suppressed, and the measurement error can be reduced. Specifically, when the direct conflict of the measuring target gas 30 onto the pressure sensors 454 and 455 is prevented, the influence of the dynamic pressure is reduced, and the detection accuracy can be prevented from being deteriorated. Then, when the direct conflict of the measuring target gas 30 onto the temperature and humidity sensor 452 is prevented, it is possible to prevent the resistance from being lowered due to the attachment of the water droplet or the pollutant.

Figure 13B:
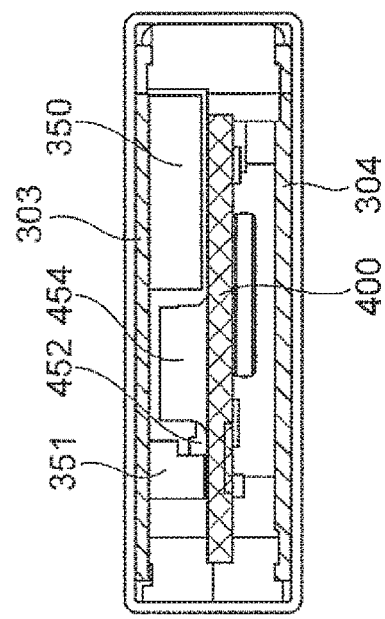
Figure 13A:
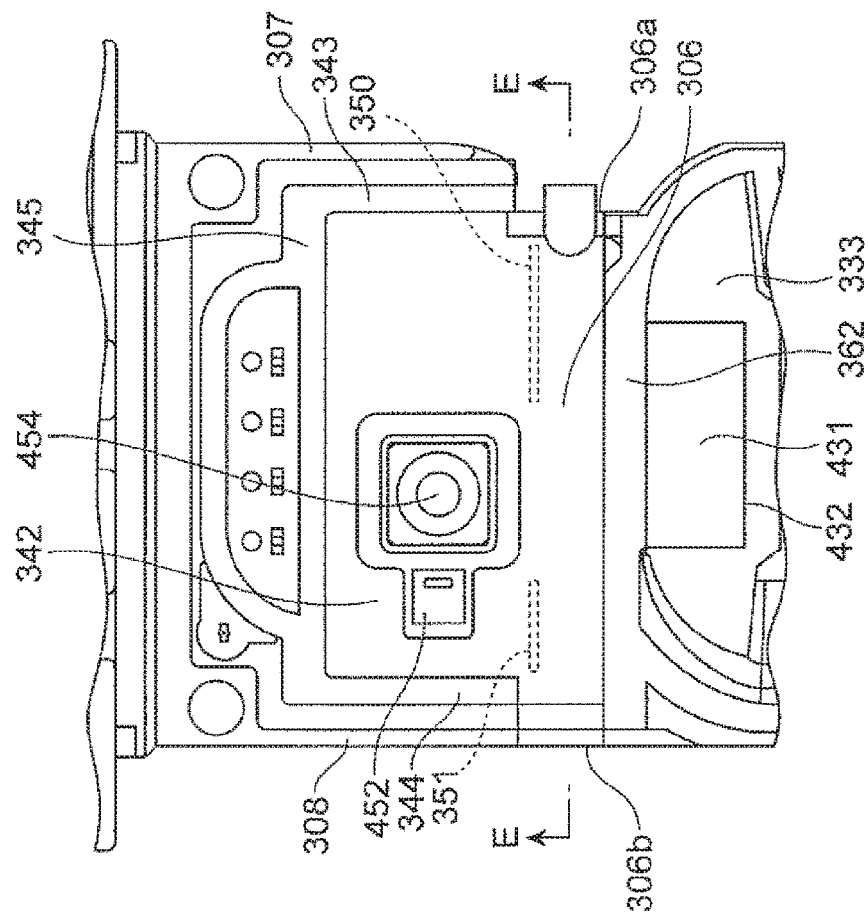

FIGS. 13(a) and 13(b) illustrate an example in which the temperature and humidity sensor 452 and the pressure sensor 454 are mounted in the rear surface of the printed circuit board 400. FIG. 13(a) is an enlarged view of the sensor chamber 342, and FIG. 13(b) is a cross-sectional view taken along a line E-E of FIG. 13(a). As illustrated in FIGS. 13(a) and 13(b), the projection 350 on the upstream side is provided between the second bypass passage inlet 306a and the pressure sensor 454, and is formed by a thin plate to be extended in the flowing direction of the measuring target gas 30. The symbols, configurations, and effects already described will be omitted herein. In this embodiment, since the number of pressure sensors is reduced by 1 compared to FIGS. 12(a) and 12(b), the length of the projection 350 on the upstream side is made longer to bury the corresponding space.

Figure 14B:
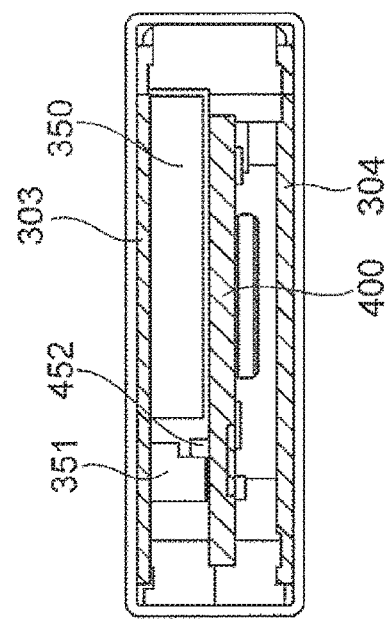
Figure 14A:
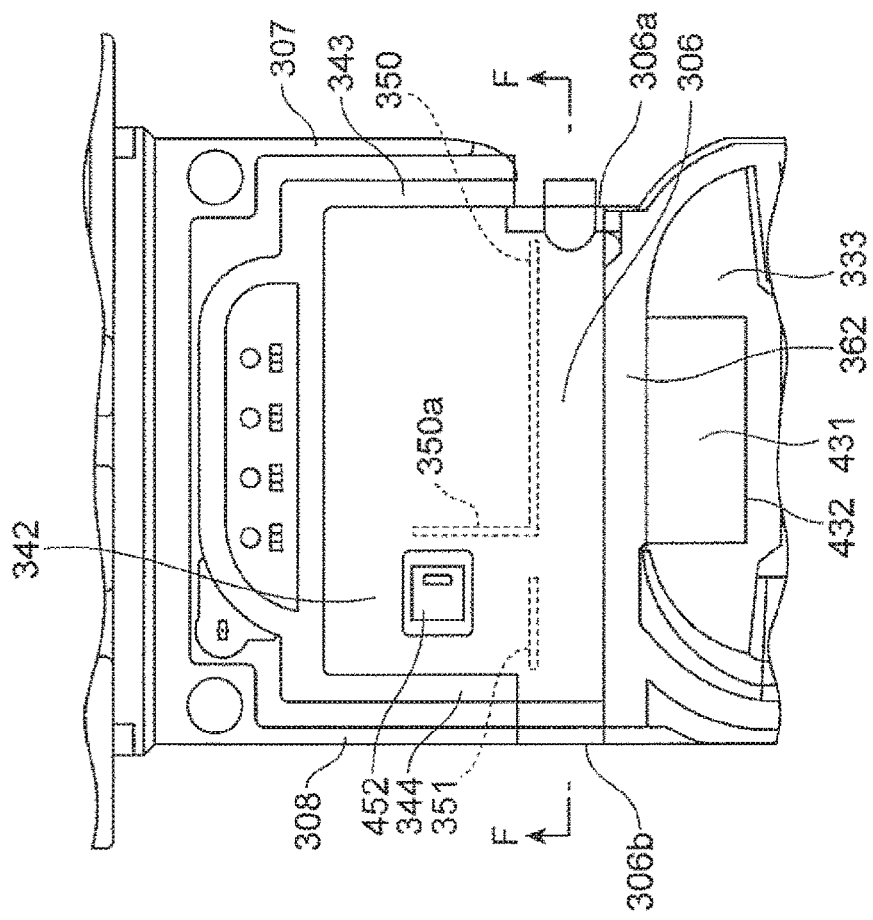

FIGS. 14(a) and 14(b) show an example in which the temperature and humidity sensor 452 is mounted in the rear surface of the printed circuit board 400. FIG. 14(a) is an enlarged view of the sensor chamber 342, and FIG. 14(b) is a cross-sectional view taken along a line F-F of FIG. 14(a). As illustrated in FIGS. 14(a) and 14(b), the projection 350 on the upstream side is provided between the second bypass passage inlet 306a and the temperature and humidity sensor 452, and is configured by a thin plate which is extended in the flowing direction of the measuring target gas 30, bent before the temperature and humidity sensor 452, and extended in a direction intersecting with the flowing of the measuring target gas 30.

In this embodiment, the temperature and humidity sensor 452 is mounted at a position separated by a certain distance from the partition 307 on the upstream side of the housing 302. Therefore, the projection 350 on the upstream side of the cover 304 is configured by a thin plate 350a of a shape intersecting with the flowing of the measuring target gas 30 in order to achieve the same effect as that of the partition 307. Therefore, it is possible to suppress the water droplet or the pollutant mixed in the air passing through the second bypass passage 306 from coming into direct conflict with the sensor. The output variation of the sensor caused by the staining and deterioration or by the water droplet can be suppressed, so that the measurement error can be reduced.

4. Signal Processing of Physical Quantity Detection Device 300

Figure 15:
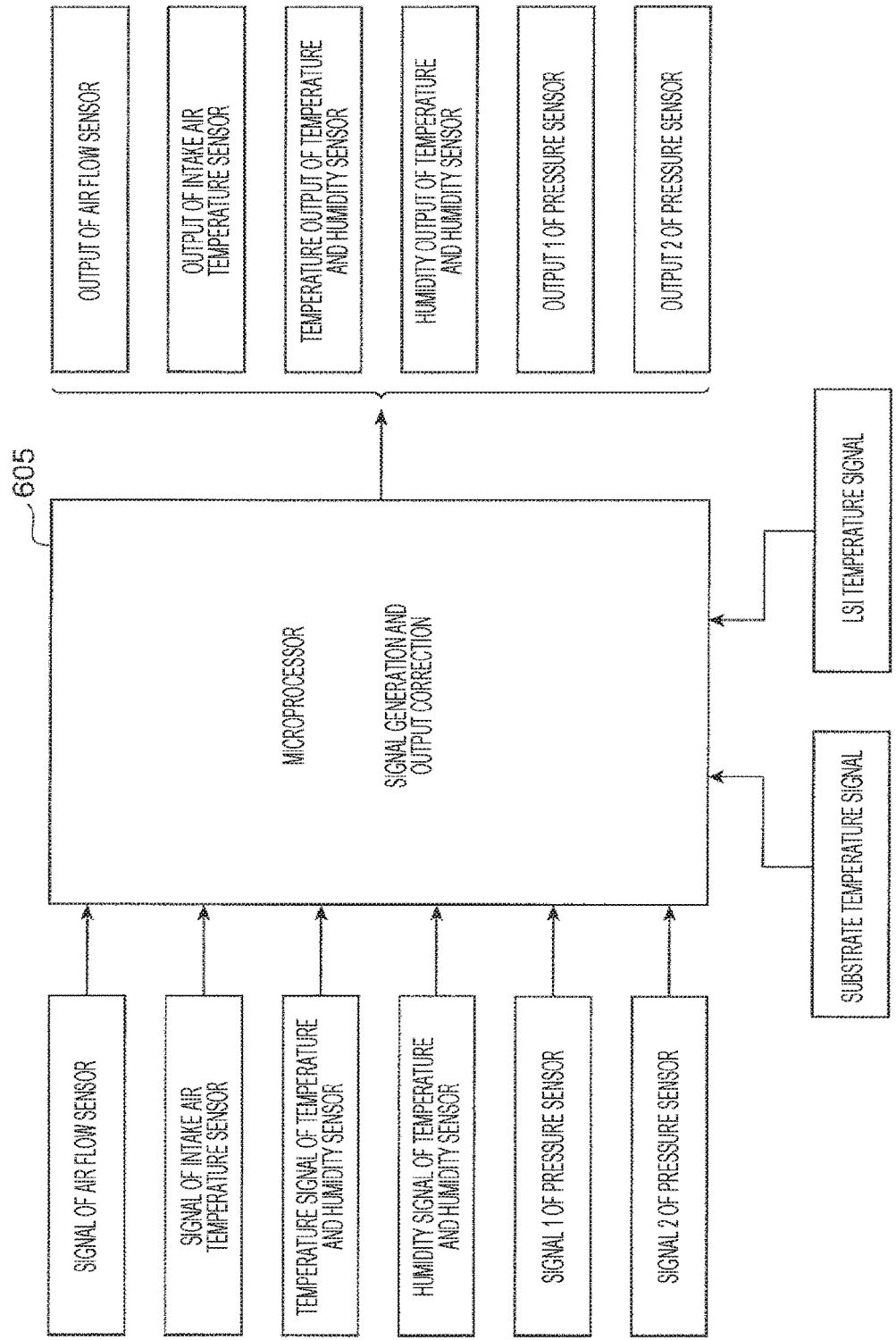
FIG. 15 is a diagram for describing inputs/outputs of the physical quantity detection device.

An input-output relation of a signal of the physical quantity detection device 300 is illustrated in FIG. 15. In this embodiment, the front surface and the rear surface of one printed circuit board 400 are both mounted with the physical quantity detection sensor, and the substrate is miniaturized. Therefore, even in the signal processing, one microprocessor 605 is used to take all the signals from the respective physical quantity sensors in order to make an electronic circuit component small, and the signals readable by the control device 200 is generated and corrected. In addition, as illustrated in FIGS. 5 and 7, an electrical signal in the printed circuit board 400 is transferred to the control device 200 through an AL wire 324 and the external terminal 323.

5. Conclusion.

According to the physical quantity detection device of this embodiment, the detection sensors 451 to 456 are mounted on one surface and the other surface of the printed circuit board 400, so that the printed circuit board 400 can be miniaturized. With the miniaturization of the printed circuit board 400, the casing part of the physical quantity detection device 300 can be also miniaturized. Therefore, a space is secured in the engine room, or a pressure loss in the intake pipe is reduced.

In addition, in this embodiment, a part of the printed circuit board 400 forms a part of the second bypass passage 306. Therefore, the other surface of the printed circuit board 400 is exposed to the air flowing in the second bypass passage 306. In other words, the self-heating generated by the circuit component such as the microprocessor 605 mounted one surface of the printed circuit board 400 is transferred to the other surface of the printed circuit board 400. Furthermore, since the heat is transferred to the air flowing in the second bypass passage 306, it is possible to suppress the heating of the entire printed circuit board 400.

Hitherto, the description has been made about embodiments of the invention, but the invention is not limited to the embodiments. Various changes in design can be made within a scope not departing from the spirit of the invention described in the accompanying claims. For example, the embodiments are described in a clearly understandable way for the invention, and thus the invention is not necessarily to provide all the configurations described above. In addition, some configurations of a certain embodiment may be replaced with the configurations of another embodiment, and the configuration of the other embodiment may also be added to the configuration of a certain embodiment. Furthermore, additions, omissions, and substitutions may be made on some configurations of each embodiment using other configurations.

REFERENCE SIGNS LIST 24 exhaust gas
30 measuring target gas
110 internal combustion engine
112 engine cylinder
114 engine piston
116 intake valve
118 exhaust valve
122 air cleaner
124 main passage
126 throttle body
128 intake manifold
132 throttle valve
144 throttle angle sensor
146 rotation angle sensor
148 oxygen sensor
152 fuel injection valve
154 ignition plug
156 idle air control valve
200 control device
300 physical quantity detection sensor
302 housing
303 front cover
304 rear cover
305 first bypass passage
305*a* first bypass passage inlet
305*b* first bypass passage outlet
306 second bypass passage
306*a* second bypass passage inlet
306*b* second bypass passage outlet
307 partition on upstream side of housing
308 partition on downstream side of housing
309 partition
311 flange
312 lower surface facing main passage 124
313 recess
314 screw hole
315 abutting portion
321 external connecting portion
322 connector
322*a* plug-in hole
323 external terminal
324 AL wire
332 front-side bypass passage groove
333 opening
334 rear-side bypass passage groove
334*a* steep slope portion
336 upstream outer wall
338 downstream external wall
341 circuit chamber
342 sensor chamber
350 projection on upstream side of cover
351 projection on downstream side of cover
400 printed circuit board
430 measurement flow-passage surface
431 measurement flow-passage rear surface
436 heat transfer surface exposing portion
450 protrusion portion
451 temperature detection unit
452 temperature and humidity sensor
453 temperature sensor
454 pressure sensor
455 pressure sensor
456 flow rate detection unit
605 circuit component (microprocessor)

The invention claimed is:

1. A physical quantity detection device that detects a plurality of physical quantities of a measuring target gas flowing in a main passage, comprising:
    a housing that is disposed in the main passage;
    a printed circuit board that is formed to be inserted in the housing;
    a plurality of detection sensors that are mounted on one surface and the other surface of the printed circuit board;
    a first bypass passage through which the measuring target gas is taken in from a first bypass passage inlet opened to the housing, and the measuring target gas is discharged from a first bypass passage outlet opened to the housing;
    a second bypass passage through which the measuring target gas is taken in from a second bypass passage inlet opened to the housing, and the measuring target gas is discharged from a second bypass passage outlet opened to the housing, wherein
    at least one detection sensor among the plurality of detection sensors is disposed in the first bypass passage, and at least one detection sensor different from the detection sensor is disposed in the second bypass passage,
    the printed circuit board includes
        a detection sensor surface region in one surface of the printed circuit board in which the detection sensor is disposed, and
        a circuit component surface region in which circuit components other than the detection sensor are disposed,
    a facing surface region is provided in another surface of the printed circuit board adjacent to the circuit component surface region, and
    at least a part of the facing surface region among the other surface of the printed circuit board is exposed to the second bypass passage.

2. The physical quantity detection device according to claim 1,
    wherein the second bypass passage is configured in cooperation with the housing, the printed circuit board, and a cover bonded to the housing.

3. The physical quantity detection device according to claim 2,
    wherein the second bypass passage is extended in parallel along a flowing direction of the measuring target gas flowing in the main passage, and the detection sensor is disposed at a position separated to a direction intersecting with a straight line connecting the second bypass passage inlet and the second bypass passage outlet.

4. The physical quantity detection device according to claim 2,
wherein the cover includes a partition wall that partitions the second bypass passage into a passage portion connecting the second bypass passage inlet and the second bypass passage outlet, and a sensor chamber where the detection sensor is disposed.

5. The physical quantity detection device according to claim 4,
wherein the housing includes a partition at a position on an upstream side of the measuring target gas from the detection sensor of the second bypass passage.

6. The physical quantity detection device according to claim 4,
wherein the housing includes a partition at a position on a downstream side of the measuring target gas from the detection sensor of the second bypass passage.

7. The physical quantity detection device according to claim 1,
wherein the detection sensors each disposed in the first bypass passage and in the second bypass passage detect different types of physical quantities.

8. The physical quantity detection device according to claim 1,
wherein a detection sensor is disposed to be wire-bonded to one surface of the printed circuit board.

* * * * *